US009801667B2

(12) United States Patent
Hawkes et al.

(10) Patent No.: US 9,801,667 B2
(45) Date of Patent: Oct. 31, 2017

(54) INSTRUMENTS, TOOLS, AND METHODS FOR PRESSON PEDICLE SCREWS

(71) Applicant: Nexus Spine, LLC, Salt Lake City, UT (US)

(72) Inventors: David Hawkes, Pleasant Grove, UT (US); Quentin Aten, Draper, UT (US)

(73) Assignee: Nexus Spine, L.L.C., Salt Lake City, UT (US)

( * ) Notice: Subject to any disclaimer, the term of this patent is extended or adjusted under 35 U.S.C. 154(b) by 0 days.

(21) Appl. No.: 14/757,080

(22) Filed: Nov. 16, 2015

(65) Prior Publication Data
US 2017/0135735 A1    May 18, 2017

(51) Int. Cl.
| A61B 17/70 | (2006.01) |
| B25B 23/10 | (2006.01) |
| A61B 17/88 | (2006.01) |

(52) U.S. Cl.
CPC ...... *A61B 17/7082* (2013.01); *A61B 17/7076* (2013.01); *A61B 17/7086* (2013.01); *A61B 17/8888* (2013.01); *B25B 23/101* (2013.01)

(58) Field of Classification Search
CPC ... B25B 23/101; B25B 23/105; B25B 23/106; B25B 23/108; A61B 17/8875; A61B 17/7082
See application file for complete search history.

(56) References Cited

U.S. PATENT DOCUMENTS

| 1,507,645 | A | * | 9/1924 | Wedgeworth | B25B 13/54 81/444 |
| 2,301,590 | A | * | 11/1942 | Signorelli | B25B 23/106 411/406 |
| 2,360,054 | A | * | 10/1944 | Haas | B25B 27/143 29/227 |
| 2,530,763 | A | * | 11/1950 | Gearhart | B25B 23/106 81/443 |
| 2,657,724 | A | * | 11/1953 | Shaff | B25B 23/106 81/444 |
| 2,781,807 | A | * | 2/1957 | Labbee | B25B 23/105 81/444 |
| 3,208,489 | A | * | 9/1965 | Walker | B25B 15/005 81/443 |

(Continued)

*Primary Examiner* — Ellen C Hammond
*Assistant Examiner* — Stuart S Bray
(74) *Attorney, Agent, or Firm* — Kirton McConkie; Adam D. Stevens

(57) ABSTRACT

Instruments, tools, and methods assist in assembling components of a surgical construct, for example, a press-on rod to a pedicle screw. A includes an elongate driving rod having a distal tip adapted to engage and transfer a rotational force to a surgical screw and a driver connection at a proximate end thereof, a first elongate shaft having a distal end, a proximal end, and a generally U-shaped channel adapted to receive the elongate driving rod therein, and a retention mechanism to retain the elongate driving rod in the generally U-shaped channel. A tool includes an elongate hollow rod having a collapsible distal tip, an elongate shaft slidingly disposed within the elongate hollow rod, the elongate shaft having a distal end comprising a driving feature, and a locking mechanism to prevent the distal end of the elongate shaft from being inadvertently removed from the distal tip of the elongate hollow rod.

10 Claims, 21 Drawing Sheets

(56) References Cited

U.S. PATENT DOCUMENTS

| | | | | |
|---|---|---|---|---|
| 3,288,184 A * | 11/1966 | Kyser | B25B 15/005 | 81/443 |
| 3,390,561 A * | 7/1968 | Finck, Jr. | E05B 19/20 | 29/268 |
| 3,604,487 A * | 9/1971 | Gilbert | A61B 17/861 | 411/403 |
| 3,825,048 A * | 7/1974 | Triska | B25B 23/106 | 81/444 |
| 4,553,455 A * | 11/1985 | Wilcox | B25B 9/02 | 81/111 |
| 4,877,020 A * | 10/1989 | Vich | A61B 17/28 | 606/86 R |
| 5,025,688 A * | 6/1991 | Davis | B25B 23/105 | 81/444 |
| 5,139,499 A * | 8/1992 | Small | A61B 17/864 | 606/104 |
| 5,605,080 A * | 2/1997 | Pfefferle | A61B 17/8891 | 81/438 |
| 6,302,001 B1 * | 10/2001 | Karle | B25B 23/108 | 81/13 |
| 6,554,834 B1 * | 4/2003 | Crozet | A61B 17/7082 | 606/272 |
| 7,921,753 B2 * | 4/2011 | Chen | B25B 13/06 | 81/444 |
| 8,231,635 B2 * | 7/2012 | Sharifi-Mehr | A61B 17/7032 | 606/104 |
| 8,343,165 B2 * | 1/2013 | Berrevoets | A61B 17/8875 | 606/104 |
| 8,770,069 B2 * | 7/2014 | Draizin | B25B 15/005 | 81/103 |
| RE45,338 E * | 1/2015 | Chin | A61B 17/7032 | 606/246 |
| 9,649,139 B2 * | 5/2017 | Sharifi-Mehr | A61B 17/7082 | |
| 9,649,140 B1 * | 5/2017 | Doose | A61B 17/7086 | |
| 9,655,665 B2 * | 5/2017 | Perrow | A61B 17/8875 | |
| 9,655,709 B2 * | 5/2017 | Kelly | A61F 2/0063 | |
| 9,681,961 B2 * | 6/2017 | Prevost | A61F 2/4611 | |
| 2002/0091386 A1 * | 7/2002 | Martin | A61B 17/7037 | 606/278 |
| 2002/0193807 A1 * | 12/2002 | Chen | A61B 17/068 | 606/129 |
| 2006/0129164 A1 * | 6/2006 | Berberich | A61B 17/8875 | 606/104 |
| 2007/0068349 A1 * | 3/2007 | Min | B25B 13/481 | 81/436 |
| 2007/0106123 A1 * | 5/2007 | Gorek | A61B 1/32 | 600/210 |
| 2007/0239159 A1 * | 10/2007 | Altarac | A61B 17/025 | 606/86 A |
| 2008/0041196 A1 * | 2/2008 | Companioni | A61B 17/862 | 81/453 |
| 2008/0115633 A1 * | 5/2008 | Sweat | B25B 13/5083 | 81/444 |
| 2008/0119857 A1 * | 5/2008 | Potash | A61B 17/7032 | 606/300 |
| 2008/0215061 A1 * | 9/2008 | Schumacher | B25B 23/108 | 606/104 |
| 2008/0269768 A1 * | 10/2008 | Schwager | B25B 23/108 | 606/104 |
| 2009/0038446 A1 * | 2/2009 | Ensign | B25B 13/44 | 81/451 |
| 2009/0275994 A1 * | 11/2009 | Phan | A61B 17/7064 | 606/86 A |
| 2009/0326545 A1 * | 12/2009 | Schaffhausen | A61B 17/8891 | 606/104 |
| 2010/0016905 A1 * | 1/2010 | Greenhalgh | A61B 17/8858 | 606/313 |
| 2011/0098715 A1 * | 4/2011 | Laubert | A61B 17/861 | 606/104 |
| 2012/0150190 A1 * | 6/2012 | Rabiner | A61B 17/1615 | 606/100 |
| 2012/0247284 A1 * | 10/2012 | Murray | B25B 15/005 | 81/436 |
| 2012/0253355 A1 * | 10/2012 | Murray | A61B 17/8888 | 606/104 |
| 2013/0074657 A1 * | 3/2013 | Bishop | B25B 23/101 | 81/53.1 |
| 2013/0331892 A1 * | 12/2013 | Peterson | A61B 17/0218 | 606/279 |
| 2014/0324062 A1 * | 10/2014 | Heuer | A61B 17/7082 | 606/104 |
| 2015/0089787 A1 * | 4/2015 | Schon | B25B 15/008 | 29/426.5 |
| 2015/0183096 A1 * | 7/2015 | Wang | B25B 23/101 | 81/455 |
| 2015/0257798 A1 * | 9/2015 | Biedermann | A61B 17/7076 | 606/86 A |
| 2015/0257807 A1 * | 9/2015 | Strnad | A61B 17/8615 | 606/308 |
| 2017/0135733 A1 * | 5/2017 | Donner | A61B 17/7055 | |

* cited by examiner

INSTRUMENTS, TOOLS, AND METHODS FOR PRESSON PEDICLE SCREWS

CROSS-REFERENCE TO RELATED APPLICATIONS

This application claims the benefit of U.S. Provisional Application No. 62/078,859, filed Nov. 12, 2014, and U.S. Provisional Application No. 62/078,865, filed Nov. 12, 2014, both of which are incorporated by reference in their entireties for all they disclose. This application is also related to the following U.S. patent applications, each of which are incorporated herein by reference in their entireties for all they disclose: U.S. patent application Ser. No. 11/952,709, filed Dec. 7, 2007, U.S. patent application Ser. No. 12/711,131, filed Feb. 23, 2010, U.S. patent application Ser. No. 13/455,854, filed Apr. 25, 2012, U.S. patent application Ser. No. 14/060,753, filed Oct. 23, 2013, U.S. patent application Ser. No. 14/555,573, filed Nov. 26, 2014, and U.S. patent application Ser. No. 14/854,029, filed Sep. 14, 2015. To the extent any teachings in these previous applications are inconsistent with the teachings of the present application, the teachings of the previous applications are to be considered subordinate to the teachings set forth herein.

BACKGROUND OF THE INVENTION

1. Field of the Invention

The present invention relates generally to the field of coupling systems for surgical implants, and more particularly to instruments, tools, and methods for use in installing components of such systems during surgical procedures.

2. Background and Related Art

The use of bone stabilization/fixation devices to align or position bones is well established. Furthermore, the use of spinal bone stabilization/fixation devices to align or position specific vertebrae or a region of the spine is well established. Typically such devices use a coupling assembly to connect or link two or more surgical screws and/or pedicle screws together to stabilize the bone and/or joint around which the screws are fixed. The coupling assembly typically is comprised of a relatively rigid member such as a plate or a rod that is used to couple or join adjacent structures or parts of the anatomy. Once the coupled structures are spatially fixed in position, procedures can be completed, healing can proceed, and the like.

Conventional surgical and/or pedicle screw coupling systems, however, have several drawbacks. Those coupling systems are rather large and bulky, which can result in more tissue damage in and around the surgical site, both from when the coupling system is installed during surgery and from implant induced, post-operative tissue irritation and erosion. The relative bulk of the prior art devices may be particularly relevant in supra-fascial applications. The prior art coupling systems have a rod-receiving device that is delivered to the surgeon already coupled or attached to the head of the surgical screw, which poses two challenges: 1) this prevents certain surgical maneuvers (e.g. placing the screws prior to interbody work); and, 2) increases the carrying cost of the inventory. Further, with traditional systems there is an inability to easily extend a fusion; that is to say that in a revision procedure the existing rod would need to be removed rather than just adding a short rod segment to the end of the coupling system. In addition, some of the prior art coupling systems include locking components (e.g., set screws and the like) that must all be carefully assembled together during the surgical procedure. Further, many traditional surgical screw system designs preclude the ability to be placed percutaneously over a guide wire, which makes these systems more difficult to install and maneuver during surgical procedures, including minimally invasive procedures.

Moreover, prior art devices require that the rod be assembled to the coupling device after the screw is inserted in the bone, which can be disadvantageous at times, whereas the option to assemble the rod to the coupling device outside the wound may prove valuable. Also, existing coupling systems necessitate simultaneous locking of all components, which prevents the ability to properly compress a coupling system along the rod because the angle relative to the surgical screw would change. Yet further still, to accommodate various anatomies and/or misplacement of surgical screws due to simple tolerance variances and/or error, requires a surgeon to bend the rod, thus further increasing cost and complexity. The tools, instruments, and methods available for use with such existing systems may be difficult and complex to use, and may require significant technical skill and experience on the part of the surgeon to achieve desired final results.

BRIEF SUMMARY OF THE INVENTION

Implementations of the invention provide instruments, tools, and methods for assembling components of a surgical construct, for example, for assembling a press-on rod to a pedicle screw. According to one implementation, a tool for use in coupling components of a surgical construct includes an elongate driving rod having a distal tip adapted to engage and transfer a rotational force to a surgical screw and a driver connection at a proximate end thereof, a first elongate shaft having a distal end, a proximal end, and a generally U-shaped channel extending along a majority of the first elongate shaft adapted to receive the elongate driving rod therein, and a retention mechanism disposed proximate the proximate end of the first elongate shaft and adapted to retain the elongate driving rod in the generally U-shaped channel.

The too may further include an elongate hollow sleeve adapted to be inserted over the driving rod and within the generally U-shaped channel while the driving rod is disposed within the generally U-shaped channel. The distal end of the first elongate shaft may include a securing tip adapted to secure a first component of a surgical construct against distal-ward movement. The elongate hollow sleeve may be adapted to press a second component of the surgical construct onto the first component of the surgical construct. The first component of the surgical construct may be a pedicle screw and the second component of the surgical construct may be a rod adapted to extend between two pedicle screws.

The tool may be adapted to permit insertion of the second component of the surgical construct over the driving rod and within and along the generally U-shaped channel of the first elongate shaft. The elongate driving rod, the first elongate shaft, and the retention mechanism may form a first guide for the second component of the surgical construct, and an additional driving rod, a second mirrored elongate shaft, and an additional retention mechanism may form a second guide for the second component of the surgical construct.

The tool may further include an actuator adapted to generate relative movement between the first elongate shaft and the elongate hollow sleeve. The actuator may be a pistol locker. The pistol locker may include a pair of handles operatively connected to a bar linkage mechanism adapted to multiply a force applied to the pair of handles and to transmit the multiplied force to generate the relative movement between the first elongate shaft and the elongate hollow sleeve.

According to another implementation, a tool for use in coupling components of a surgical construct includes an elongate hollow rod having a collapsible distal tip adapted to collapse to allow insertion into a surgical screw and further adapted to expand and engage a female cavity of the surgical screw to prevent withdrawal of the distal tip from the female cavity of the surgical screw, an elongate shaft slidingly disposed within the elongate hollow rod, the elongate shaft having a distal end comprising a driving feature adapted to engage a corresponding driving feature of the female cavity of the surgical screw, and a locking mechanism to prevent the distal end of the elongate shaft from being inadvertently removed from the distal tip of the elongate hollow rod.

The locking mechanism may include a mechanism such as corresponding snap fit engagement contours formed on the elongate hollow rod and the elongate shaft, a spring loaded push button release, a twist cam lock, a Morse taper interface, and a friction fit. The elongate hollow rod and the elongate shaft may be viewed together as forming a locking wand. The locking wand may have a proximal end having an interface for allowing a driver to transmit a rotational force to the locking wand and thus to any engaged surgical screw. The tool may also include an elongate hollow sleeve adapted to slidingly receive the locking wand therein and to permit application of a force to two components of a surgical construct via the locking wand and the elongate hollow sleeve. The two components of the surgical construct may be a pedicle screw and a rod adapted to extend between two pedicle screws.

The tool may further include an actuator adapted to generate relative movement between the locking wand and the elongate hollow sleeve. The tool may also include a mechanism to reversibly engage the locking wand to the actuator. The mechanism to reversibly engage the locking wand to the actuator may include captive bearings within the actuator and a corresponding groove on the locking wand. The actuator may be a pistol locker. The pistol locker may include a pair of handles operatively connected to a bar linkage mechanism adapted to multiply a force applied to the pair of handles and to transmit the multiplied force to generate the relative movement between the locking wand and the elongate hollow sleeve.

BRIEF DESCRIPTION OF THE SEVERAL VIEWS OF THE DRAWINGS

The objects and features of the present invention will become more fully apparent from the following description and appended claims, taken in conjunction with the accompanying drawings. Understanding that these drawings depict only typical embodiments of the invention and are, therefore, not to be considered limiting of its scope, the invention will be described and explained with additional specificity and detail through the use of the accompanying drawings in which:

DETAILED DESCRIPTION OF THE INVENTION

Figure 1:
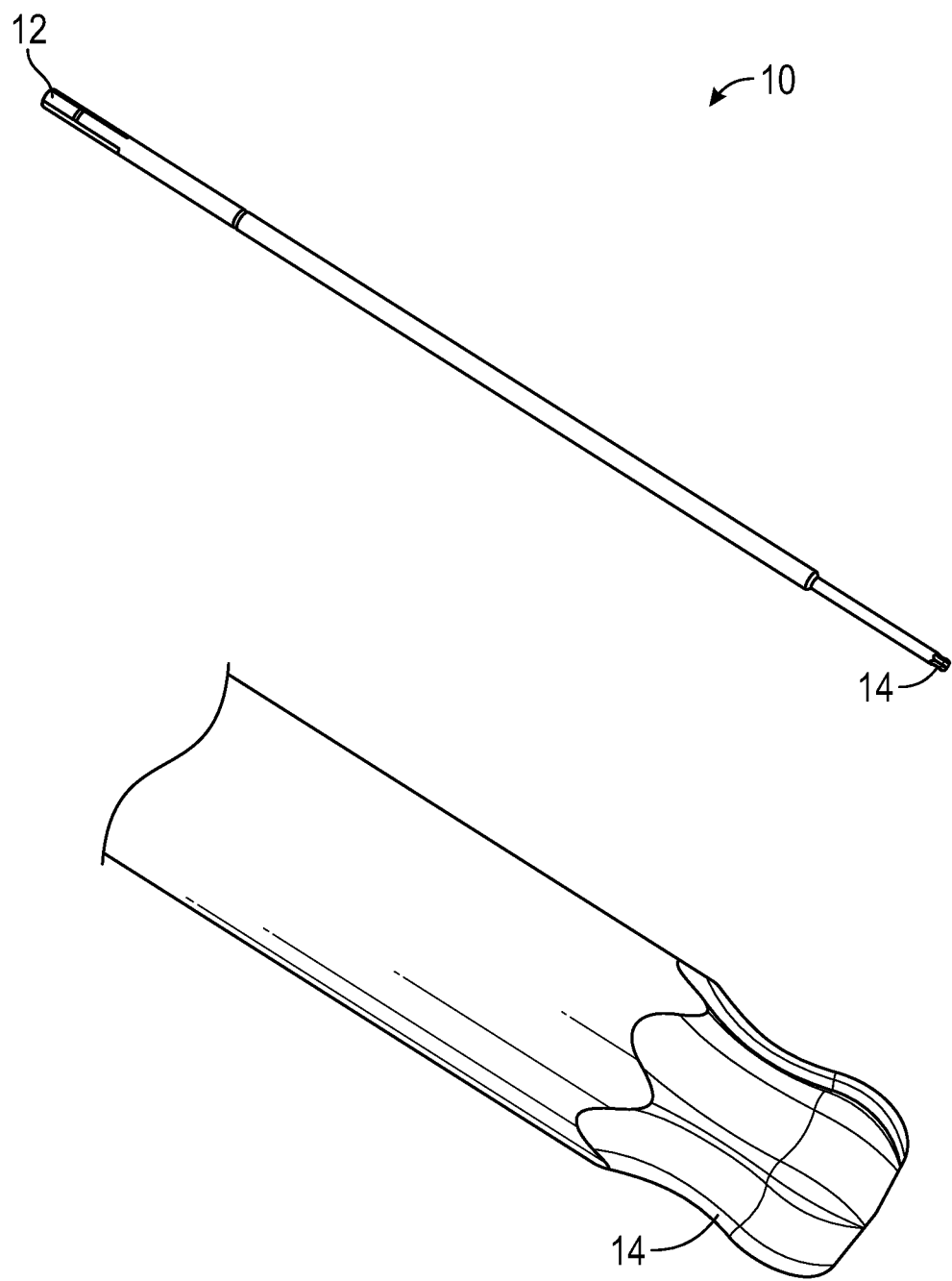
FIG. 1 shows views of an illustrative elongate driving rod.

A description of embodiments of the present invention will now be given with reference to the Figures. It is expected that the present invention may take many other forms and shapes, hence the following disclosure is intended to be illustrative and not limiting, and the scope of the invention should be determined by reference to the appended claims.

Embodiments of the invention provide instruments, tools, and methods for assembling components of a surgical construct, for example, for assembling a press-on rod to a pedicle screw. According to one embodiment, a tool for use in coupling components of a surgical construct includes an elongate driving rod having a distal tip adapted to engage and transfer a rotational force to a surgical screw and a driver connection at a proximate end thereof, a first elongate shaft having a distal end, a proximal end, and a generally U-shaped channel extending along a majority of the first elongate shaft adapted to receive the elongate driving rod therein, and a retention mechanism disposed proximate the proximate end of the first elongate shaft and adapted to retain the elongate driving rod in the generally U-shaped channel.

The too may further include an elongate hollow sleeve adapted to be inserted over the driving rod and within the generally U-shaped channel while the driving rod is disposed within the generally U-shaped channel. The distal end of the first elongate shaft may include a securing tip adapted to secure a first component of a surgical construct against distal-ward movement. The elongate hollow sleeve may be adapted to press a second component of the surgical construct onto the first component of the surgical construct. The first component of the surgical construct may be a pedicle screw and the second component of the surgical construct may be a rod adapted to extend between two pedicle screws.

The tool may be adapted to permit insertion of the second component of the surgical construct over the driving rod and within and along the generally U-shaped channel of the first elongate shaft. The elongate driving rod, the first elongate shaft, and the retention mechanism may form a first guide for the second component of the surgical construct, and an additional driving rod, a second mirrored elongate shaft, and an additional retention mechanism may form a second guide for the second component of the surgical construct.

The tool may further include an actuator adapted to generate relative movement between the first elongate shaft and the elongate hollow sleeve. The actuator may be a pistol locker. The pistol locker may include a pair of handles operatively connected to a bar linkage mechanism adapted to multiply a force applied to the pair of handles and to transmit the multiplied force to generate the relative movement between the first elongate shaft and the elongate hollow sleeve.

According to another embodiment, a tool for use in coupling components of a surgical construct includes an elongate hollow rod having a collapsible distal tip adapted to collapse to allow insertion into a surgical screw and further adapted to expand and engage a female cavity of the surgical screw to prevent withdrawal of the distal tip from the female cavity of the surgical screw, an elongate shaft slidingly disposed within the elongate hollow rod, the elongate shaft having a distal end comprising a driving feature adapted to engage a corresponding driving feature of the female cavity of the surgical screw, and a locking mechanism to prevent the distal end of the elongate shaft from being inadvertently removed from the distal tip of the elongate hollow rod.

The locking mechanism may include a mechanism such as corresponding snap fit engagement contours formed on the elongate hollow rod and the elongate shaft, a spring loaded push button release, a twist cam lock, a Morse taper interface, and a friction fit. The elongate hollow rod and the elongate shaft may be viewed together as forming a locking wand. The locking wand may have a proximal end having an interface for allowing a driver to transmit a rotational force to the locking wand and thus to any engaged surgical screw. The tool may also include an elongate hollow sleeve adapted to slidingly receive the locking wand therein and to permit application of a force to two components of a surgical construct via the locking wand and the elongate hollow sleeve. The two components of the surgical construct may be a pedicle screw and a rod adapted to extend between two pedicle screws.

The tool may further include an actuator adapted to generate relative movement between the locking wand and the elongate hollow sleeve. The tool may also include a mechanism to reversibly engage the locking wand to the actuator. The mechanism to reversibly engage the locking wand to the actuator may include captive bearings within the actuator and a corresponding groove on the locking wand. The actuator may be a pistol locker. The pistol locker may include a pair of handles operatively connected to a bar linkage mechanism adapted to multiply a force applied to the pair of handles and to transmit the multiplied force to generate the relative movement between the locking wand and the elongate hollow sleeve.

FIGS. 1-10 illustrate a system, instrument, device, tool, and/or method for coupling components of a surgical construct. Specifically, these Figures illustrate a device and method for placing spinal fusion pedicle screws and rods such as those generally disclosed in the applications incorporated herein by reference. It is envisioned that adaptations could be made to the embodiments specifically described herein to allow the instrument to work with other pedicle screw systems.

The first component of the system is illustrated in FIG. 1, which shows views of an elongate driving rod or driver 10. The driver 10 includes a shaft with a driver connection 12 (which may be a male driver connection) at a proximate end and a male driving feature 14 at a distal end. The driver connection 12 permits connection of the driver 10 to an instrument for generating rotational force, and the male driving feature 14 adapted to engage and drive a pedicle screw. The male driving feature 14 may be ball shaped to allow the driver 10 to rotate in the pedicle screw's female driving interface. In the illustrated embodiment, the male driving feature 10 is ball hexalobe, but any polyaxial driving feature, such as ball hex) is embraced by embodiments of the invention.

Figure 2:
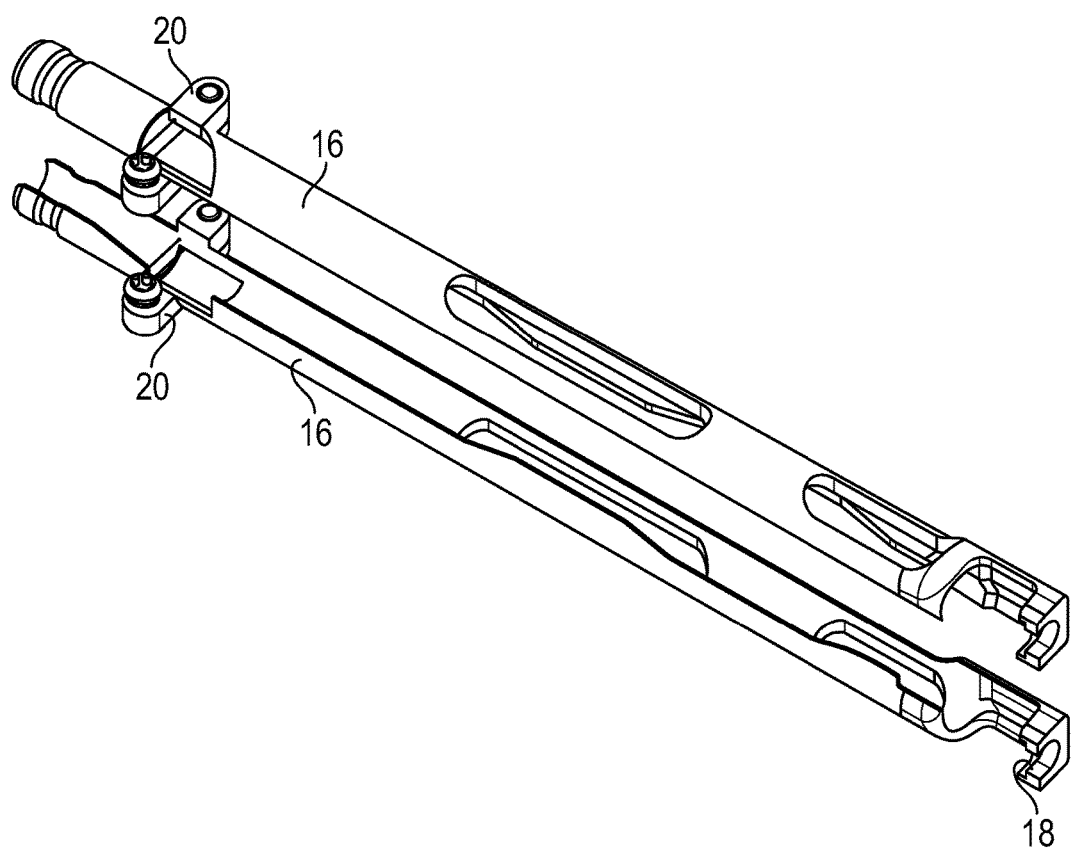
FIG. 2 shows a perspective view of illustrative mirrored elongate shafts having generally U-shaped channels.

FIG. 2 shows a perspective view of a mirrored pair of elongate shafts 16 each adapted to receive a driver 10 therein. Each shaft 16 includes a generally U-shaped channel that receives the driver 10 therein. Each shaft 16 terminates at a distal end thereof in a generally horseshoe-shaped tip 18 adapted to support the pedicle screw head as a rod coupler is pressed over the pedicle screw head to create an interference or press fit as is described in the applications incorporated by reference hereto. The open end of the generally U-shaped channel allows the rod coupler to pass through the open end of the U shape while being translated along the channel. The shafts 16 are generally used in pairs, with one being the mirror of the other as is illustrated in FIG. 2, allowing the tips 18 of each shaft 16 to be oriented in the same direction as shown in FIG. 2.

Figure 3:
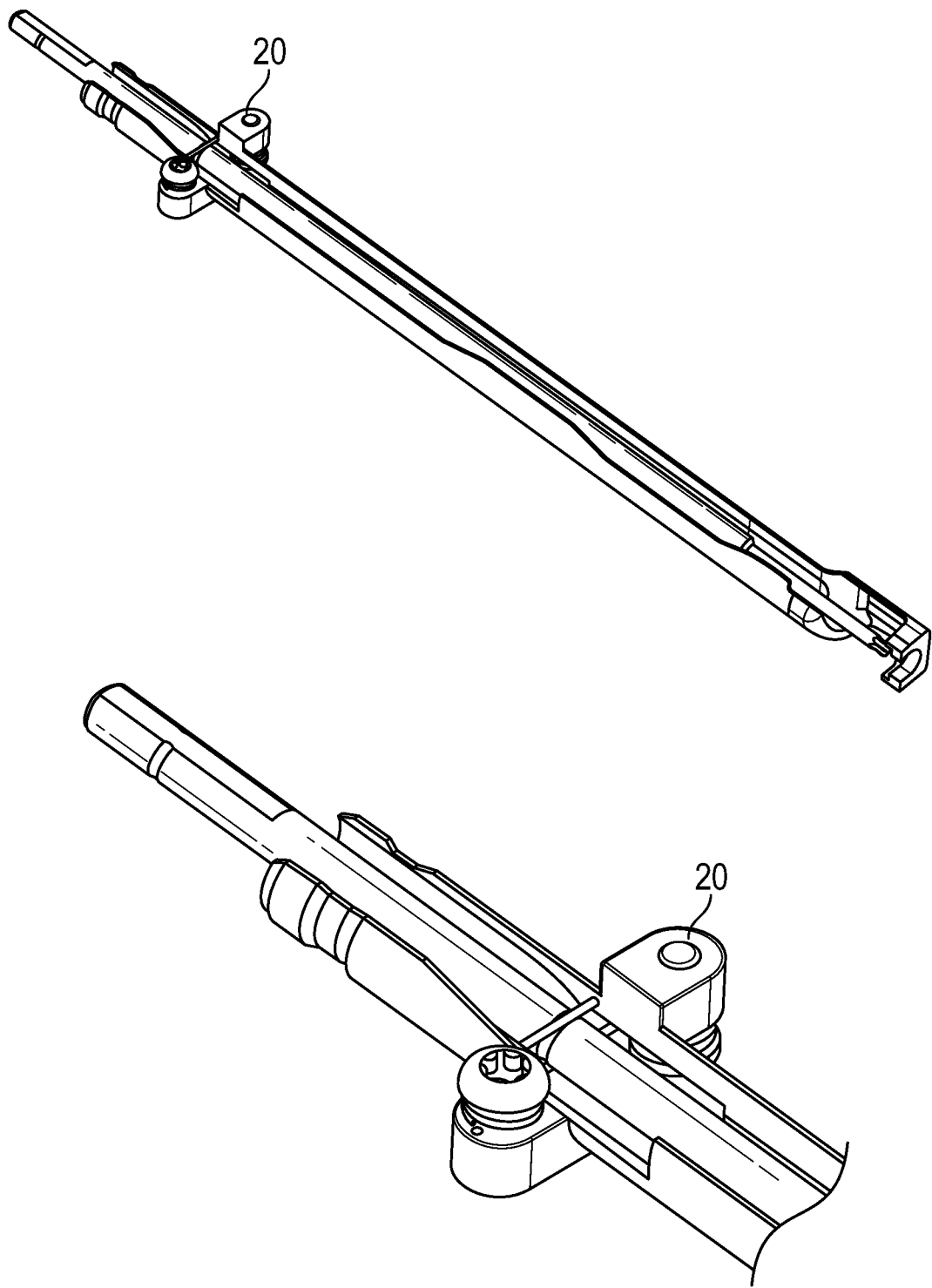
FIG. 3 shows views of an elongate driving rod disposed within a channel of an elongate shaft.

Each shaft 16 includes a retention mechanism 20 adapted to retain and center the driver 10 within the generally U-shaped channel, as is best illustrated in FIG. 3. The retention of the driver 10 within the shaft 16 also prevents the driver 10 from falling through the open side of the channel. The retention mechanism 20 allows the rod coupler and a barrel of a pistol locker to pass over the driver 10 in the generally U-shaped channel. In the illustrated embodiment, the retention mechanism 20 includes a torsional spring adapted to rest in a groove on the shaft of the driver 10, although other embodiments might include a split ring, a compliant beam, spring loaded paddles, and the like.

Figure 4:
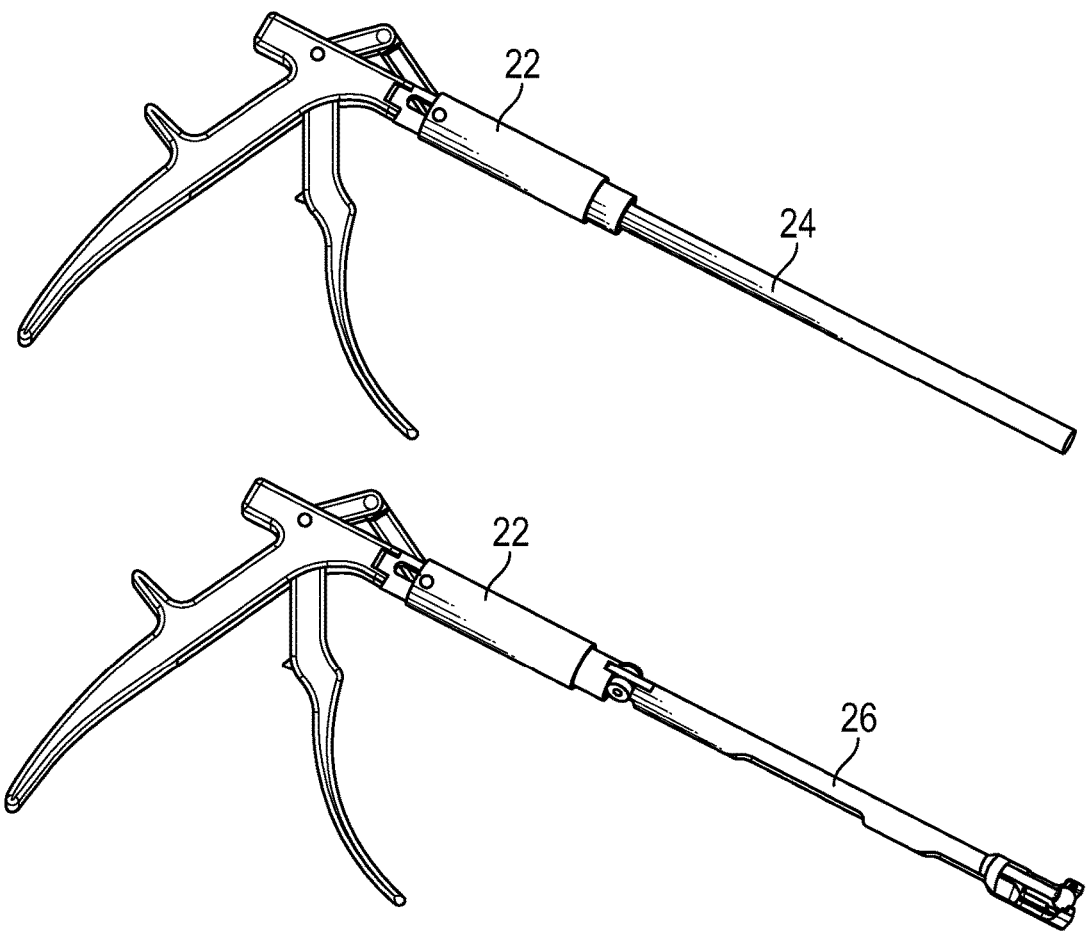
FIG. 4 shows views of a pistol locker and of a pistol locker engaged with an elongate driving rod and an elongate shaft.

FIG. 4 shows views of a pistol locker 22, which is one example of an actuator adapted to engage the shaft 16 and provide a coupling force to couple components of a surgical construct. The pistol locker 22 includes a long barrel 24 adapted to be inserted over the driver 10 while the driver rests within the generally U-shaped channel of the shaft 16, such that the barrel 24 extends between the shaft 16 and the driver 10. The pistol locker 22 includes a mechanism such as a bar linkage, that advances the barrel 24 relative to the shaft 16 so as to provide a coupling force between components of the surgical construct, e.g., between the rod coupler and the pedicle screw. The pistol locker 22 is mated to the shaft 16 and driver 10 during the locking procedure, as shown in the lower view of FIG. 4.

Figure 5B:
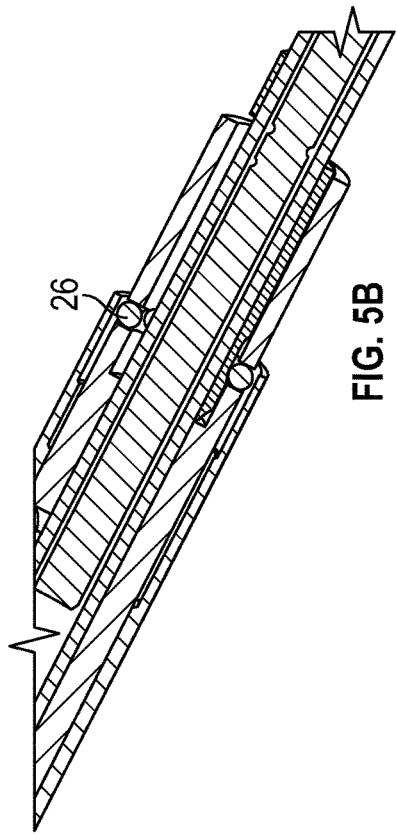
FIGS. 5A-5D shows illustrative views demonstrating engagement between a pistol locker and an elongate shaft.
Figure 5D:
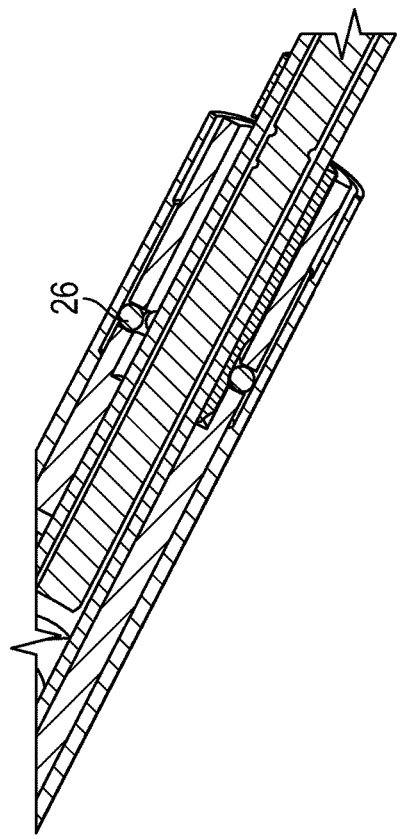
Figure 5A:
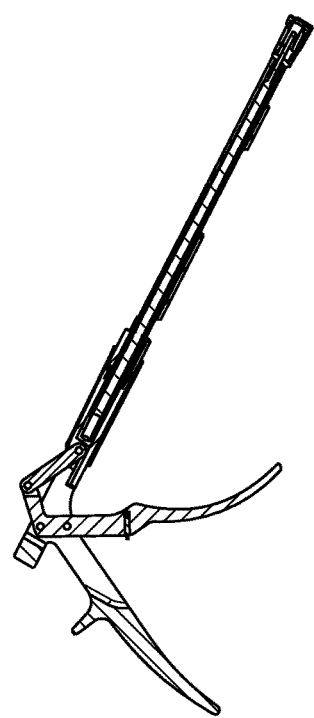
Figure 5C:
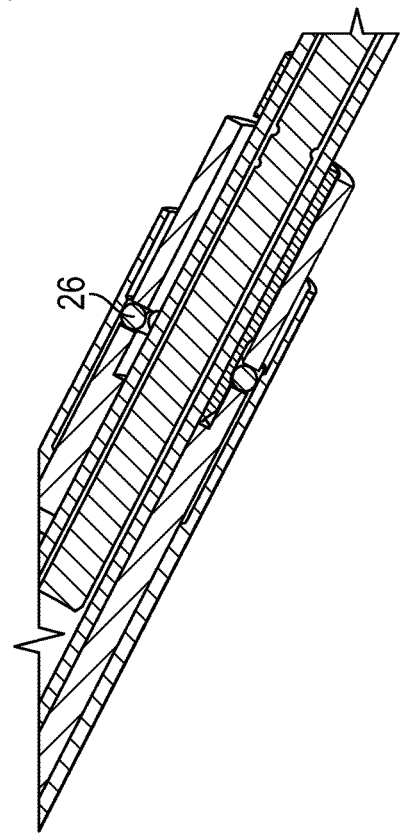

Internal to the pistol locker 22 is a mechanism which attaches the shaft 16 to the pistol locker 22, as is shown in the views of FIG. 5A-5D. A set of ball bearings 26 is captive between an outer sleeve of the pistol locker 22 and the barrel 24 of the pistol locker 22. When the pistol locker barrel 24 is placed over the driver 10 and into the generally U-shaped channel of the shaft 16, the bearings 26 are free to translate radially and to allow the shaft 16 to slide into the pistol locker 22 (FIG. 5B). Actuating the pistol locker 22 (e.g., via a handle or trigger) advances both the inner barrel 24 and the outer sleeve. As the outer sleeve advances, the ball bearings 26 become constrained between the barrel 24 and the other sleeve, and come to rest in a groove in the shaft 16 (FIGS. 5C and 5D). This type of connection allows the pistol locker 22 to rotate around the shaft 16 while remaining attached to the shaft 16.

Figure 6:
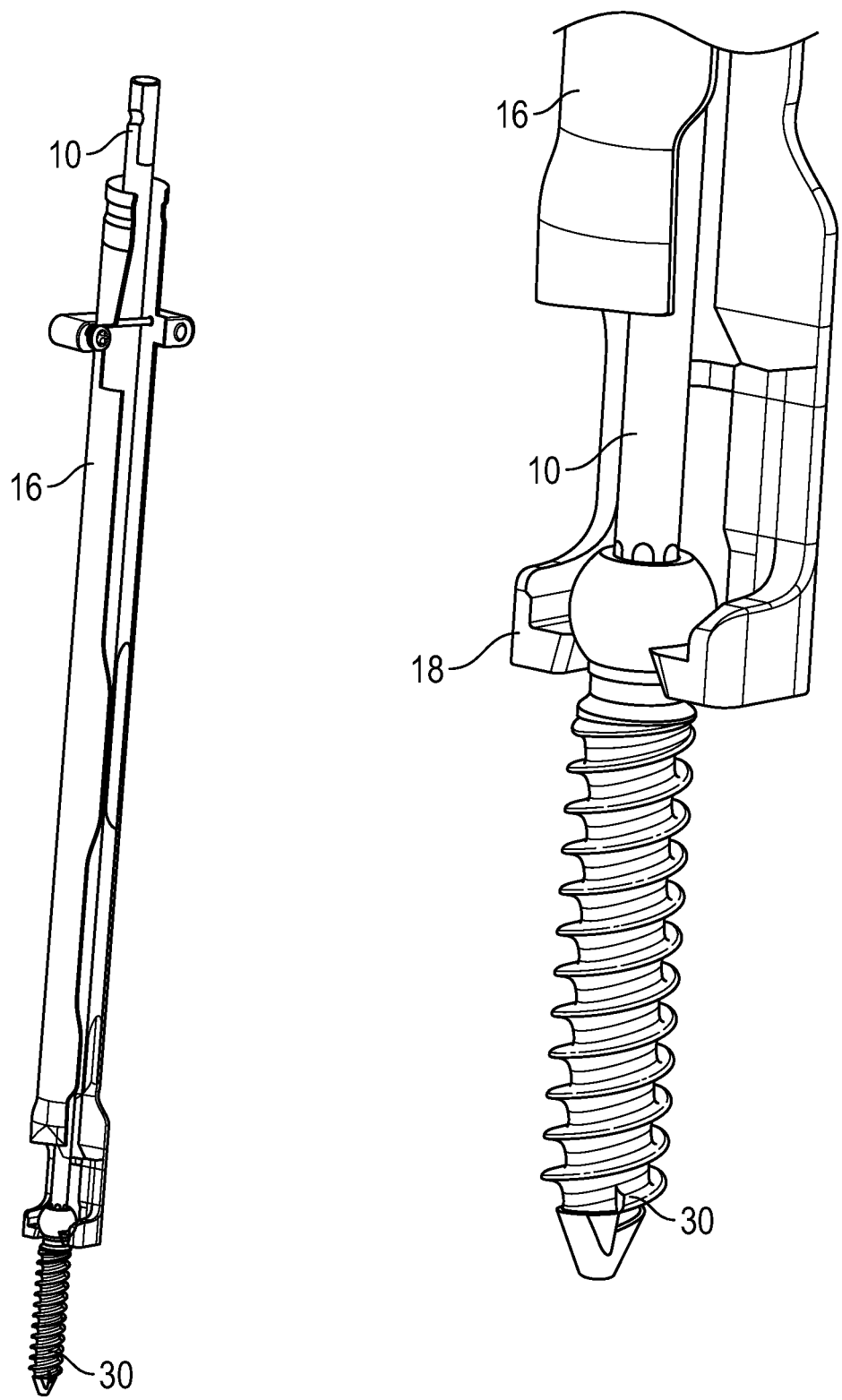
FIG. 6 shows illustrative views demonstrating engagement between a pedicle screw and an elongate driving rod inserted in an elongate shaft.
Figure 7:
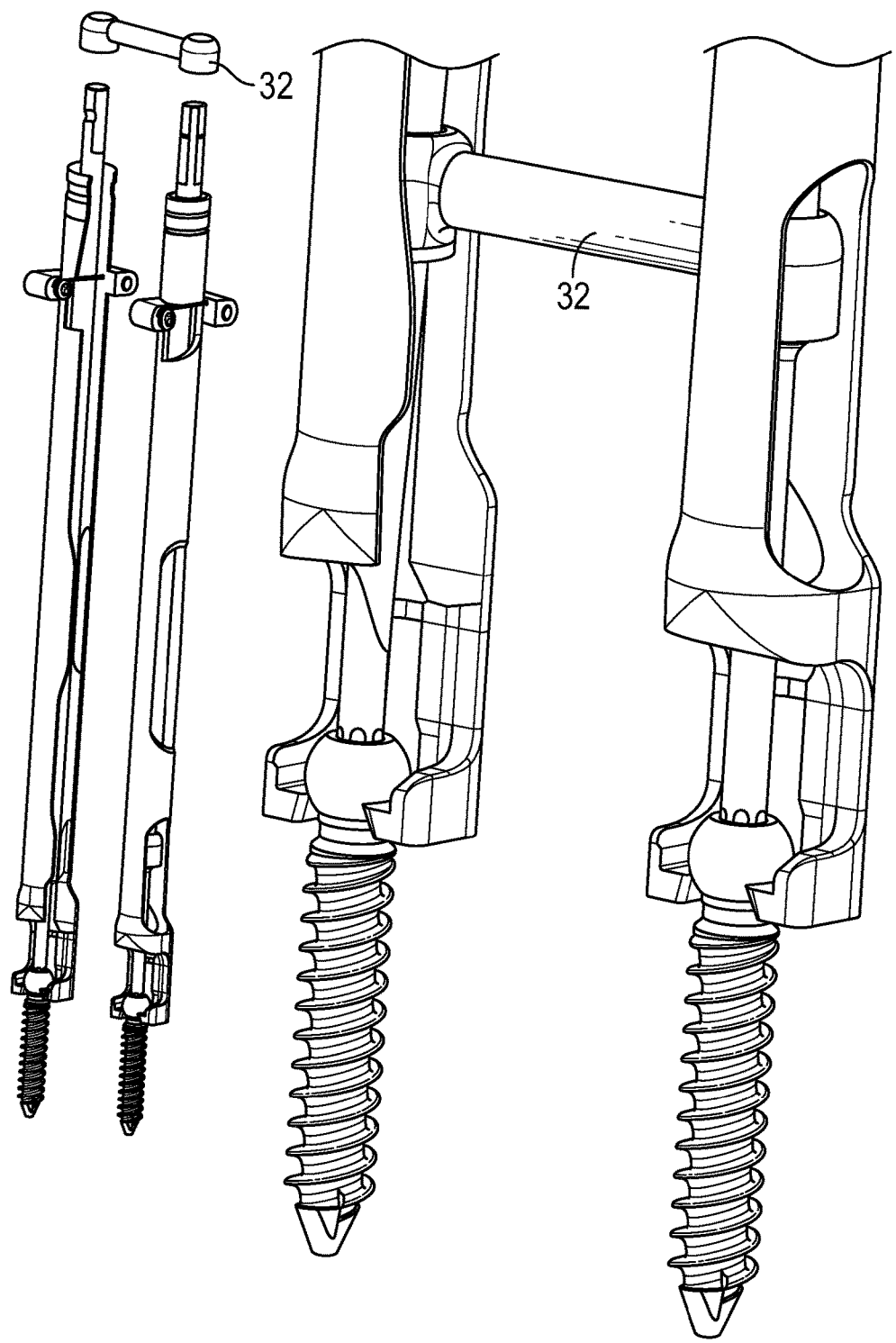
FIGS. 7-10 shows illustrative views demonstrating use of a mirrored pair of elongate driving rod-elongate shaft constructs engaged with pedicle screws, a rod adapted to extend between the surgical screws, and a pistol locker adapted generate a force to cause the rod to press on to and engage the pedicle screws.

FIGS. 6-10 illustrate how to use this embodiment of the tool to couple components of a surgical construct (e.g. a rod coupler extending between two pedicle screws). As illustrated in the views of FIG. 6, a pedicle screw 30 is inserted into the tip 18, and the driver 10 is inserted into the shaft 16 all the way until engaging a female driving feature of the pedicle screw 30. The driver is then attached to a driving device and the pedicle screw 30 is screwed in to the recipient's spine at a desired location. These steps are repeated for the second pedicle screw 30 using the mirrored shaft 16, whereupon the pair of mirrored shafts 16 will extend from the patient's back and can be aligned in parallel fashion as shown in the view of FIG. 7.

Figure 8:
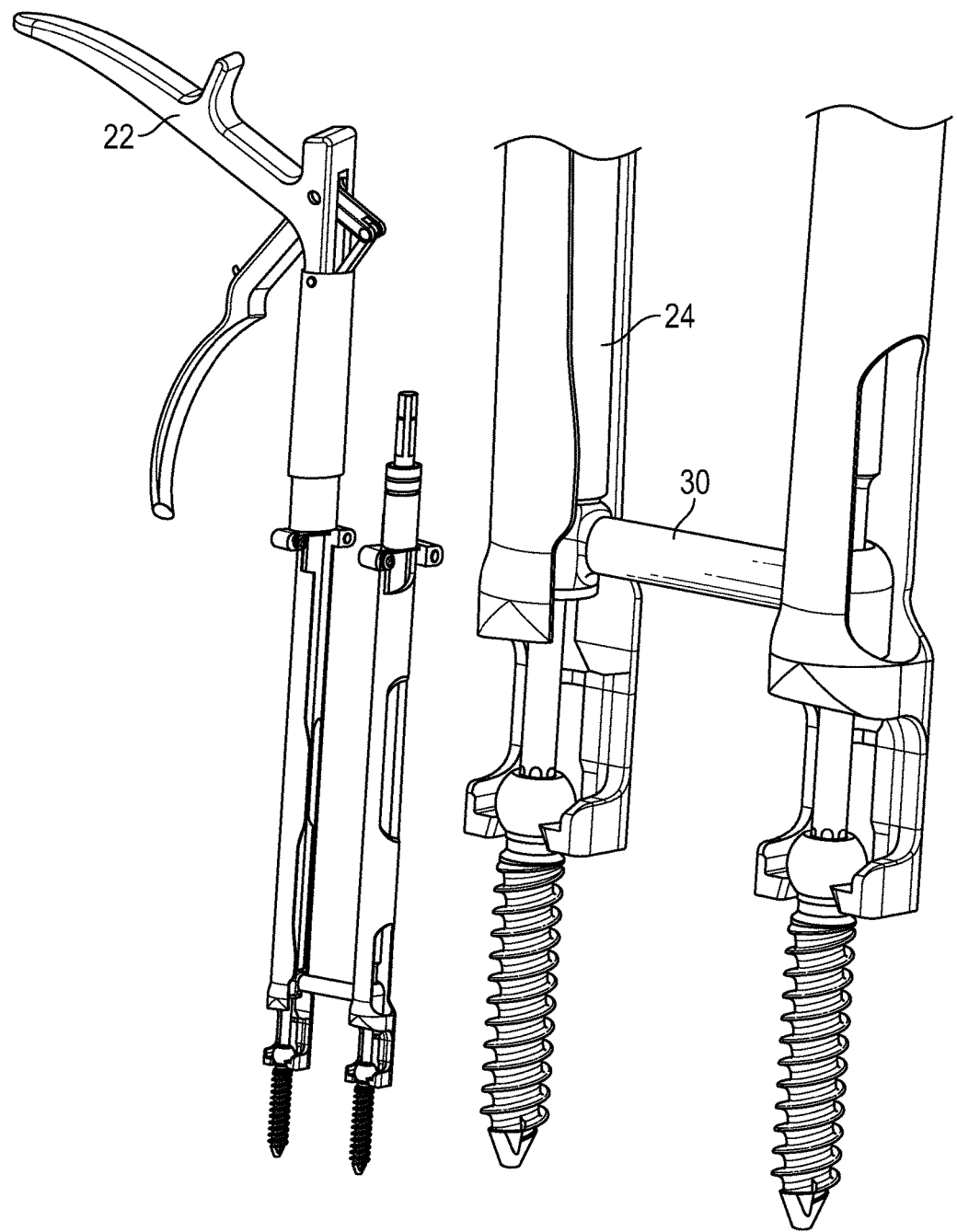
Figure 9:
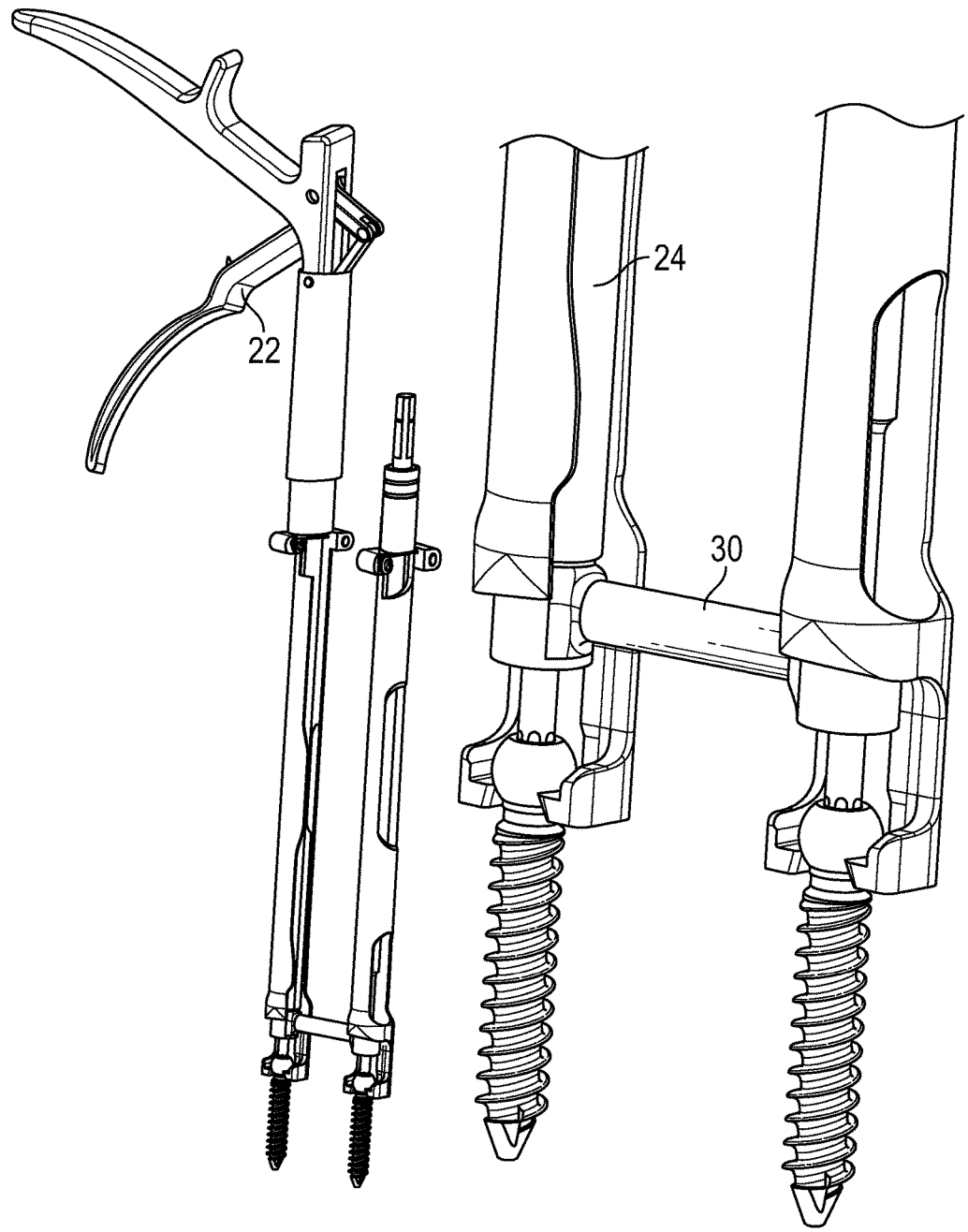

The distance between screw heads is measured using a device such as a Vernier caliper that measures the distance between the driver shafts when they are constrained to be parallel (and when the vertebrae are properly aligned). The measurement is used to select an appropriate length of rod coupler 32, which is then passed over the two drivers 10 and down the generally U-shaped channels of the pair of shafts 16, as is illustrated in FIG. 7. The barrel 24 of the pistol locker 22 is then slid over the first driver 10 and into the first generally U-shaped channel of the corresponding shaft 16 as shown in FIG. 8. The barrel 24 is advanced until it engages the rod coupler 32, which advances it further toward the pedicle screws 30 if the rod coupler 32 is not already in contact with the pedicle screws 30, as shown in FIG. 9.

Figure 10:
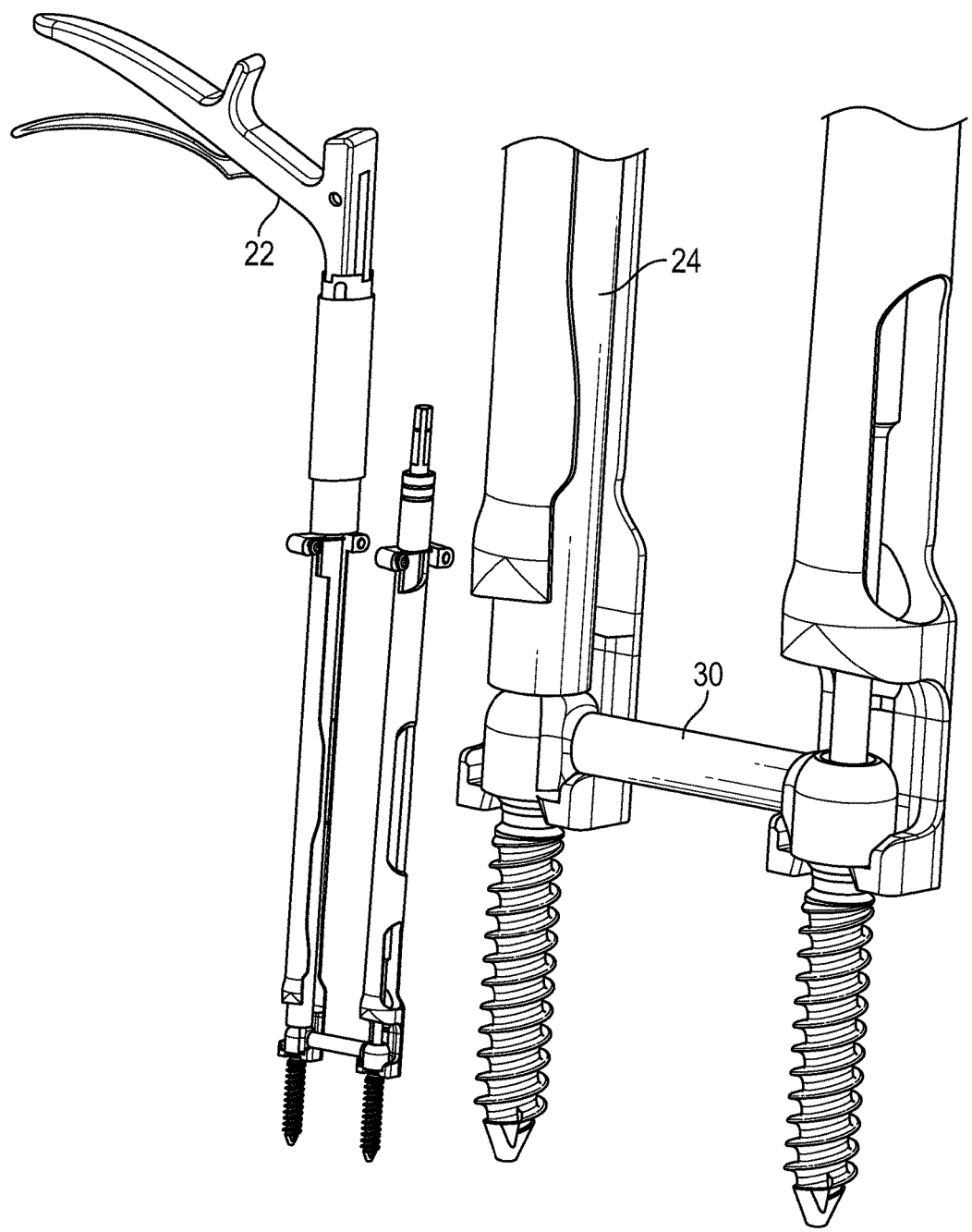

The surgeon then partially actuates the handle or trigger of the pistol locker 22 to lock the pistol locker 22 to the shaft 16 and to complete the advancement of the rod coupler 32 to the pedicle screw 30. Then the surgeon fully actuates the handle or trigger of the pistol locker 22 to press the rod coupler 32 onto the first pedicle screw 30, creating a press or interference fit between the rod coupler 32 and the pedicle screw 30 as is discussed in detail in the applications incorporated herein by reference. The surgeon then fully releases the trigger or handle of the pistol locker 22 to disengage the pistol locker from the shaft 16, moves the pistol locker to the other shaft 16 and repeats the process to press the rod coupler 32 onto the second pedicle screw, completing assembly of the surgical construct as shown in FIG. 10. The surgeon removes the pistol locker 22 from the shaft 16, removes the drivers 10 and shafts 16 from the pedicle screws 30 and completes the surgery by closing using conventional techniques.

FIGS. 11-21 illustrate a system, instrument, device, tool, and/or method for coupling components of a surgical construct. Specifically, these Figures illustrate a device and method for placing spinal fusion pedicle screws and rods such as those generally disclosed in the applications incorporated herein by reference. It is envisioned that adaptations could be made to the embodiments specifically described herein to allow the instrument to work with other pedicle screw systems.

There are two primary components of the system illustrated in FIGS. 11-21, a locking wand and a pistol locker. The locking wand serves as a screw driver for the pedicle screw, a guide for placing the rod coupler, and as part of the assembly that is used to lock the pedicle screw to the rod coupler. The locking wand may be cannulated to allow use over a guide wire, though non-cannulated embodiments are also embraced as acceptable modifications of the system.

Figure 11:
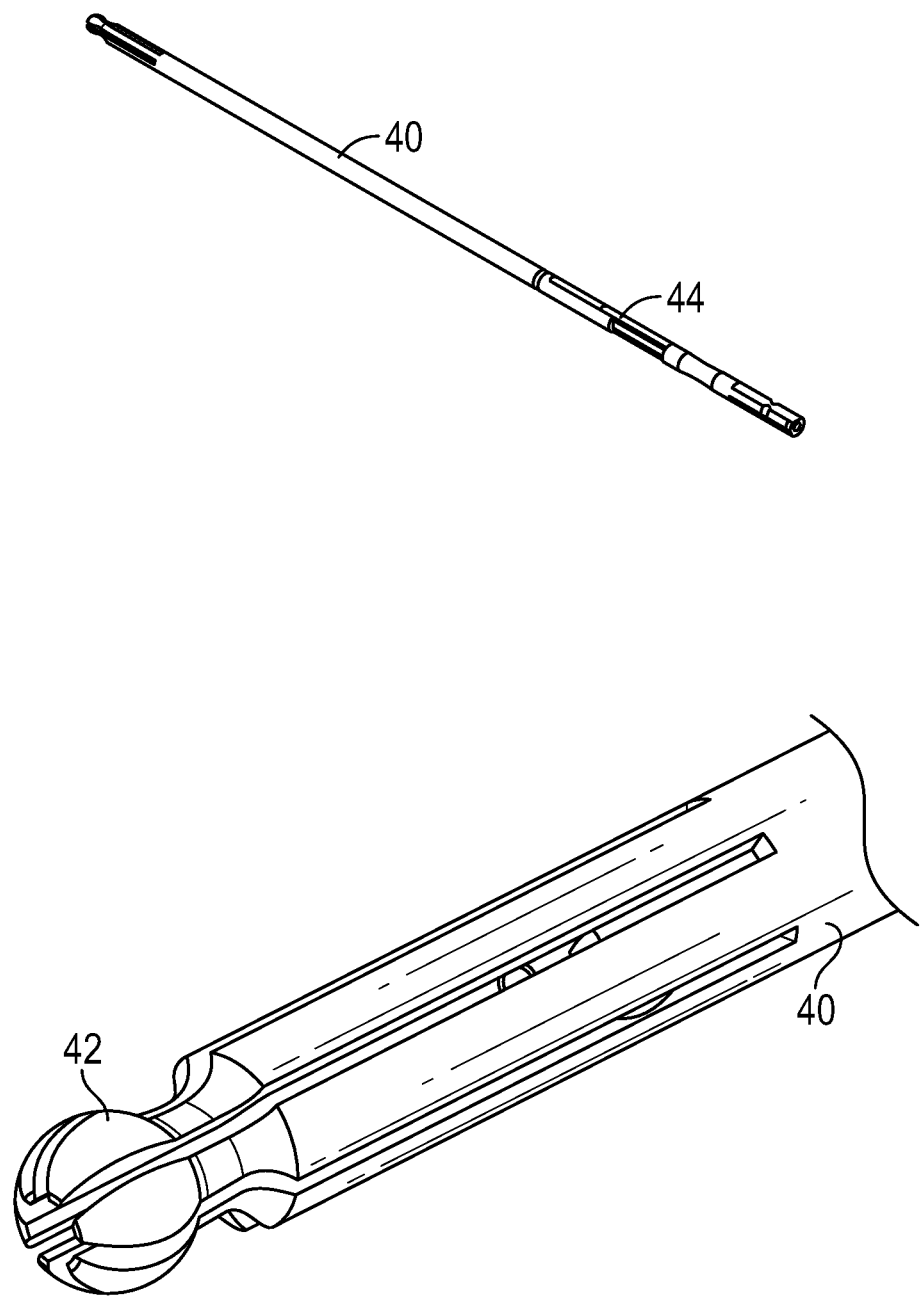
FIG. 11 shows views of an elongate hollow rod having a collapsible tip.

The illustrated locking wand includes various functional elements. The first of the functional elements hollow rod 40. The hollow rod 40 has a collapsible tip 42 on its distal end as is illustrated in FIG. 11. As is shown in FIG. 11, the collapsible tip 42 is formed of various flexible segments separated by longitudinal channels. When there is nothing backing the flexible segments, they are allowed to collapse inward, making the collapsible tip 42 collapsible so as to allow the collapsible tip 42 to be pushed into the inner female cavity of the head of a pedicle screw.

Figure 12:
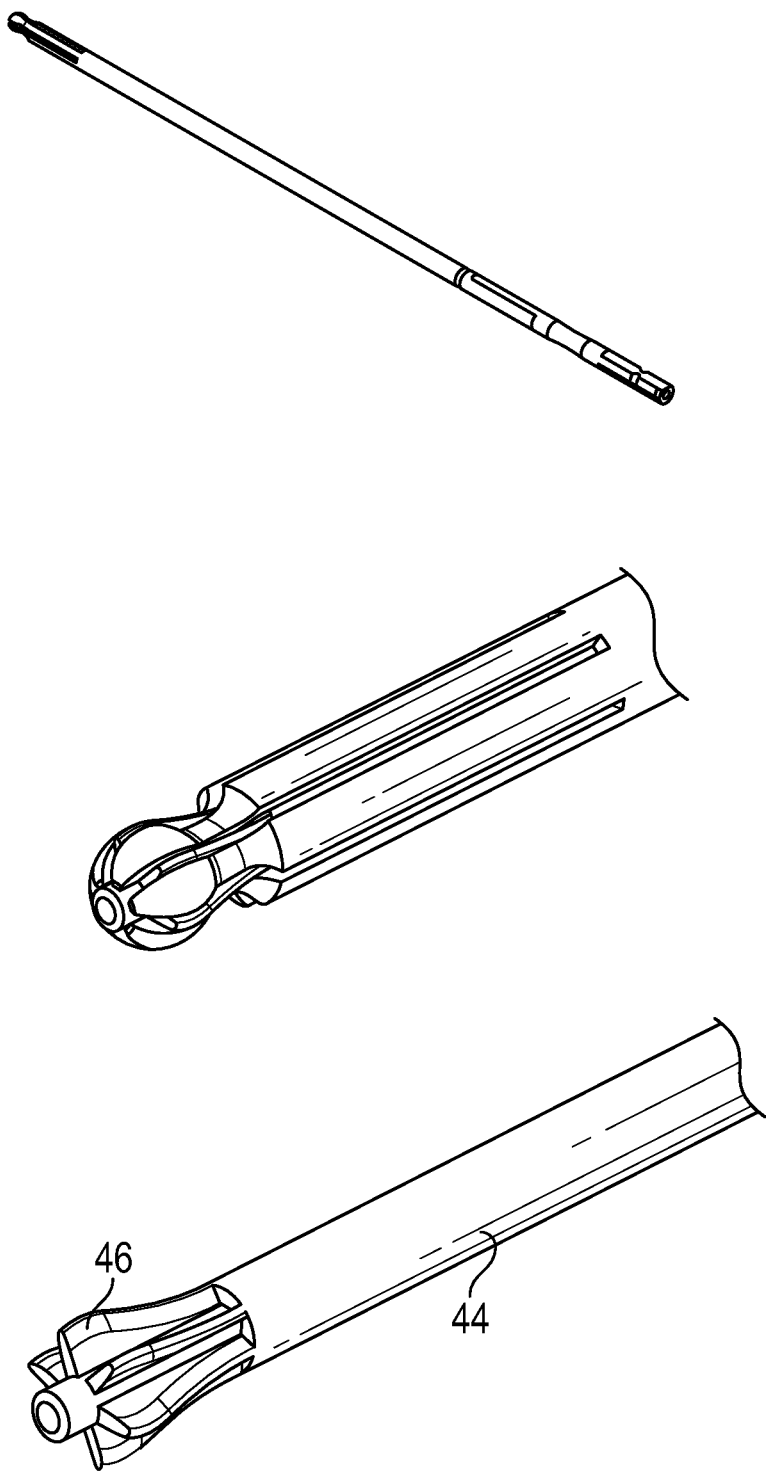
FIG. 12 shows views of an elongate shaft adapted to be disposed within an elongate hollow rod, the elongate shaft having a driving feature.

The hollow rod 40 is adapted to receive an elongate shaft 44 slidingly disposed therein, as is best illustrated in the views of FIG. 12. When the elongate shaft is slidingly moved distally within the hollow rod 40, it provides backing to the flexible segments such that they are no longer permitted to collapse inward, and the collapsible tip 42 becomes rigid in its fully expanded state, which creates a poly-axial interface with the inner female cavity of the pedicle screw, which cavity may be generally spherical.

In the illustrated embodiment, the shaft 44 terminates in a driving feature 46. The illustrated driving feature 46 is a ball hexalobe driver, which provides a poly-axial driving interface for the pedicle screw. The shaft 44 extends through the hollow rod 40 and extends from a proximal end thereof to form a driving interface adapted to engage a driving mechanism which permits application of a rotational force through the shaft 44 and rod 40 to the pedicle screw. The combination of the shaft 44 and rod 40 make up the locking wand.

When the locking wand is inserted into the pedicle screw, the shaft 44 is withdrawn proximally in the hollow rod 40. Once the collapsible tip 42 is within the pedicle screw, the shaft 44 is pushed distally relative to the hollow rod 40 until the driving feature 46 is within the pedicle screw and the collapsible tip 42. This act not only expands the collapsible tip 42, but also extends the driving feature 46 into the pedicle screw. Thus, the single action not only connects the locking wand to the pedicle screw but also simultaneously engages the locking wand's male driving feature 46 with the pedicle screw's female driving feature.

The general ball shape of the driving feature 46 allows the pedicle screw to be driven with the locking wand's axis at an angle to the axis of the pedicle screw. Additionally, the ball shape of the driving feature 46 allows the locking wand to be poly-axial with respect to the pedicle screw after the pedicle screw has been driven without disengaging the driving feature 46. Though a ball hexalobe driving feature 46 is illustrated in FIGS. 11-23, other poly-axial driving features are embraced by embodiments of the invention, including, but not limited to a friction drive between the collapsible tip 42 and the inner spherical cavity of the pedicle screw, a ball hex drive (hexagonal cross section integrated into the collapsible tip 42), and a ball cross drive.

Figure 13:
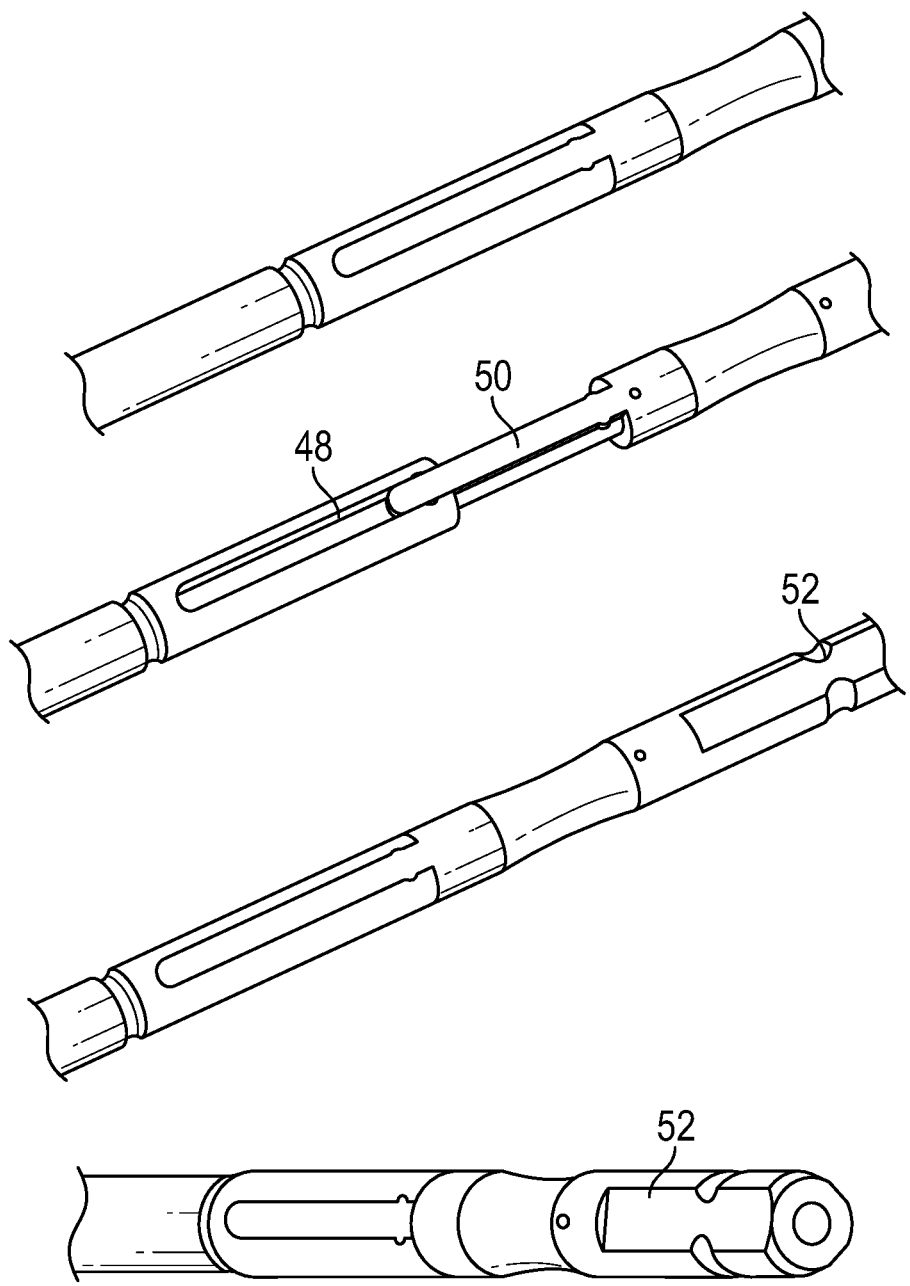
FIG. 13 shows a locking mechanism and driving feature for a elongate hollow rod and elongate shaft construct forming a locking wand.

As mentioned above, the locking wand includes an interface for attaching to a driving device, as well as for attaching to a pistol locker, as will be described in more detail below. The locking wand may also include an interface for preventing rotation of the hollow rod 40 relative to the elongate shaft 44. As illustrated in FIG. 13, this rotation-preventing interface may include a groove 48 in the hollow rod 40 and a corresponding protrusion 50 on the elongate shaft 44.

The groove 48 and protrusion 50 may optionally be shaped to provide a locking mechanism to prevent the elongate shaft 44 from inadvertently moving within the hollow rod 40. Prevention of such motion ensures that the collapsible tip 42 remains in the rigid configuration until the surgeon performs a deliberate action to allow the collapsible tip 42 to collapse and disengage from the pedicle screw. In the embodiment illustrated in FIG. 13, the locking mechanism includes a snap fit provided between barbs on the protrusion 50 and a corresponding indentation on the groove 48. Other locking mechanisms could be used, including but not limited to a spring loaded push button release, a twist cam lock, a Morse taper type interface, and a friction fit.

The proximal end of the locking wand includes an interface for attaching to a driver handle. In the embodiment illustrated in FIG. 13, the interface is shown as a tri-lobe connector 52, though other connection types are embraced as alternate embodiments, including but not limited to square drive, AO drive, and hex drive.

Figure 14:
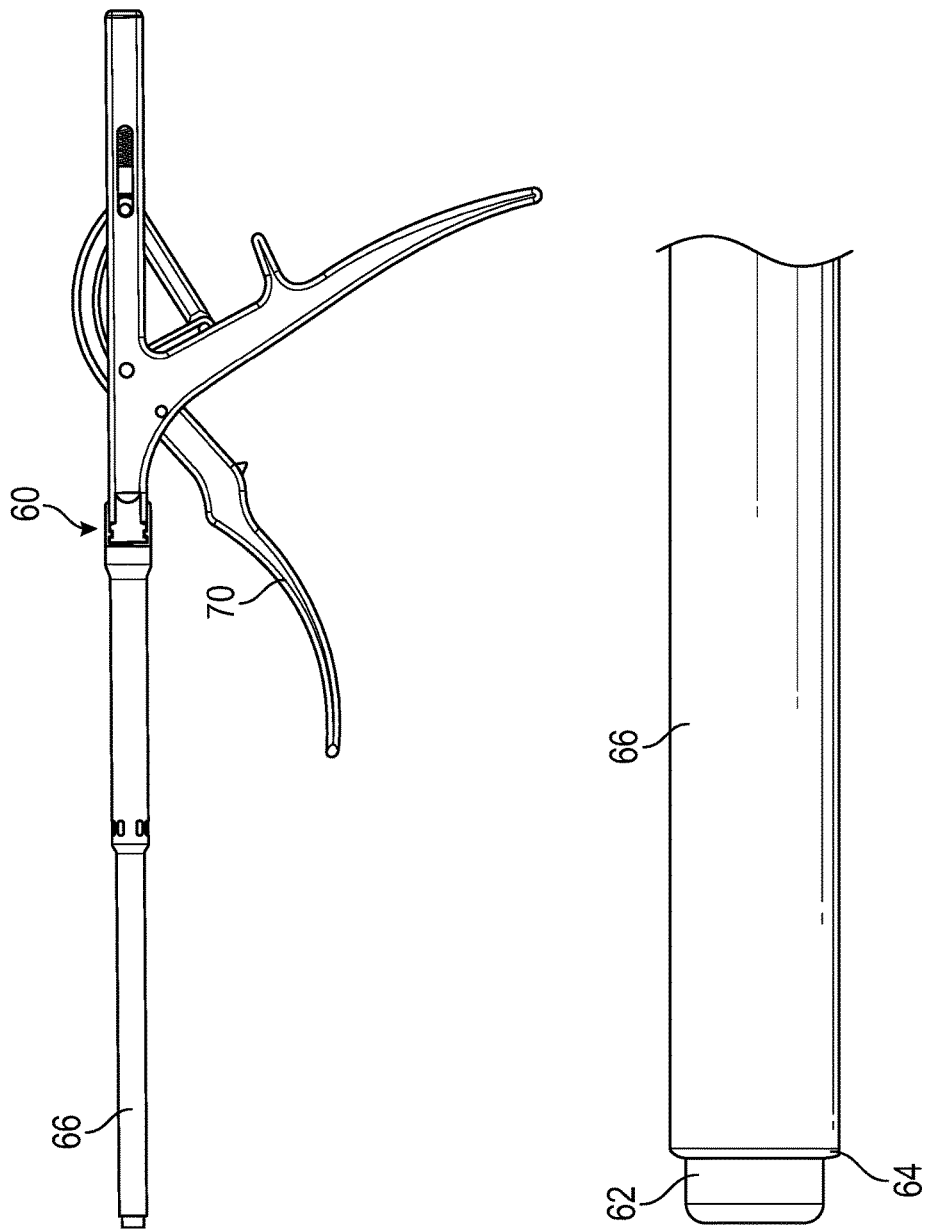
FIG. 14 shows views of a pistol locker adapted to press one component of a surgical construct on to another component of the surgical construct.
Figure 15:
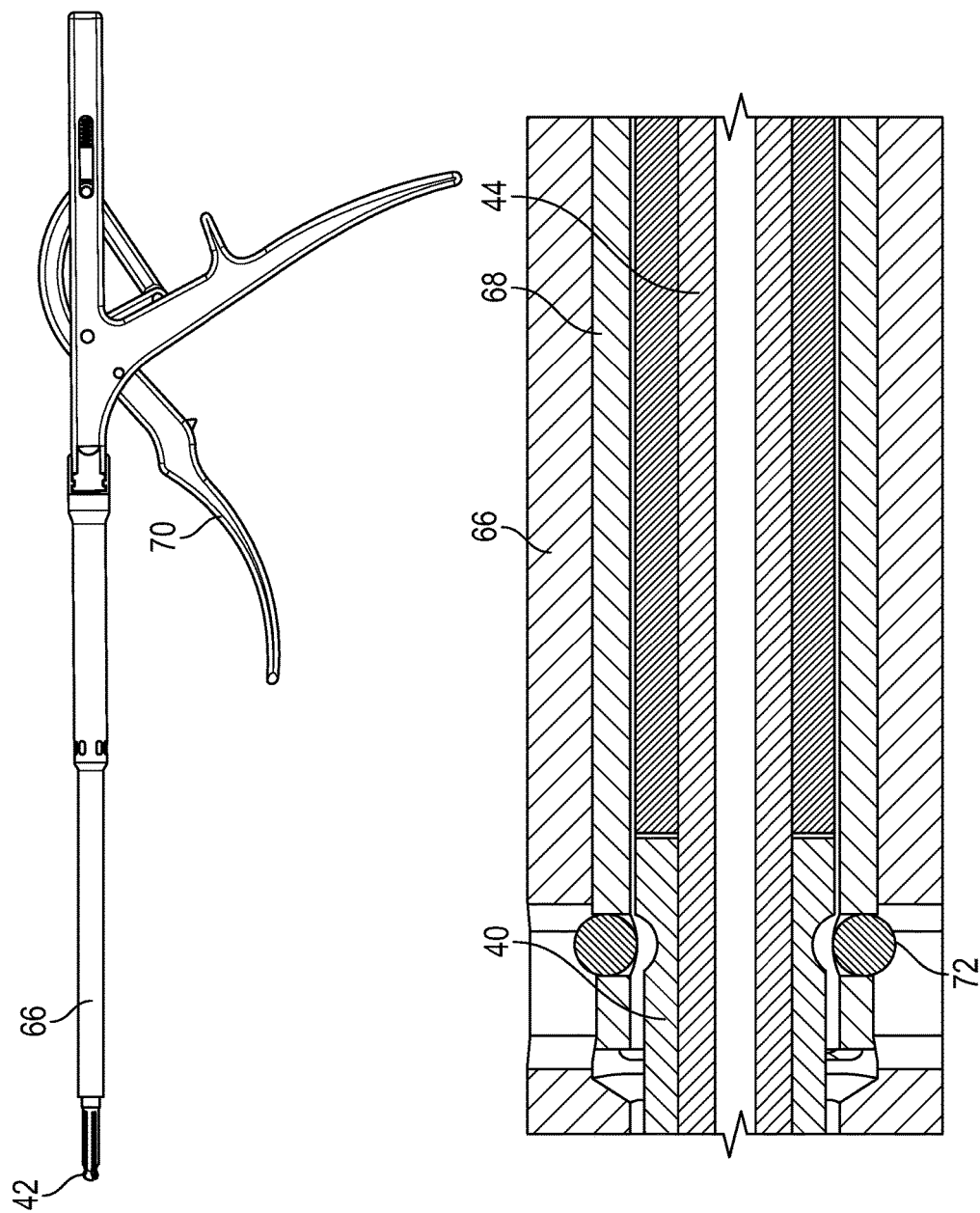
FIGS. 15-16 show views of a pistol locker demonstrating a mechanism for engagement of the pistol locker to a locking wand.
Figure 16:
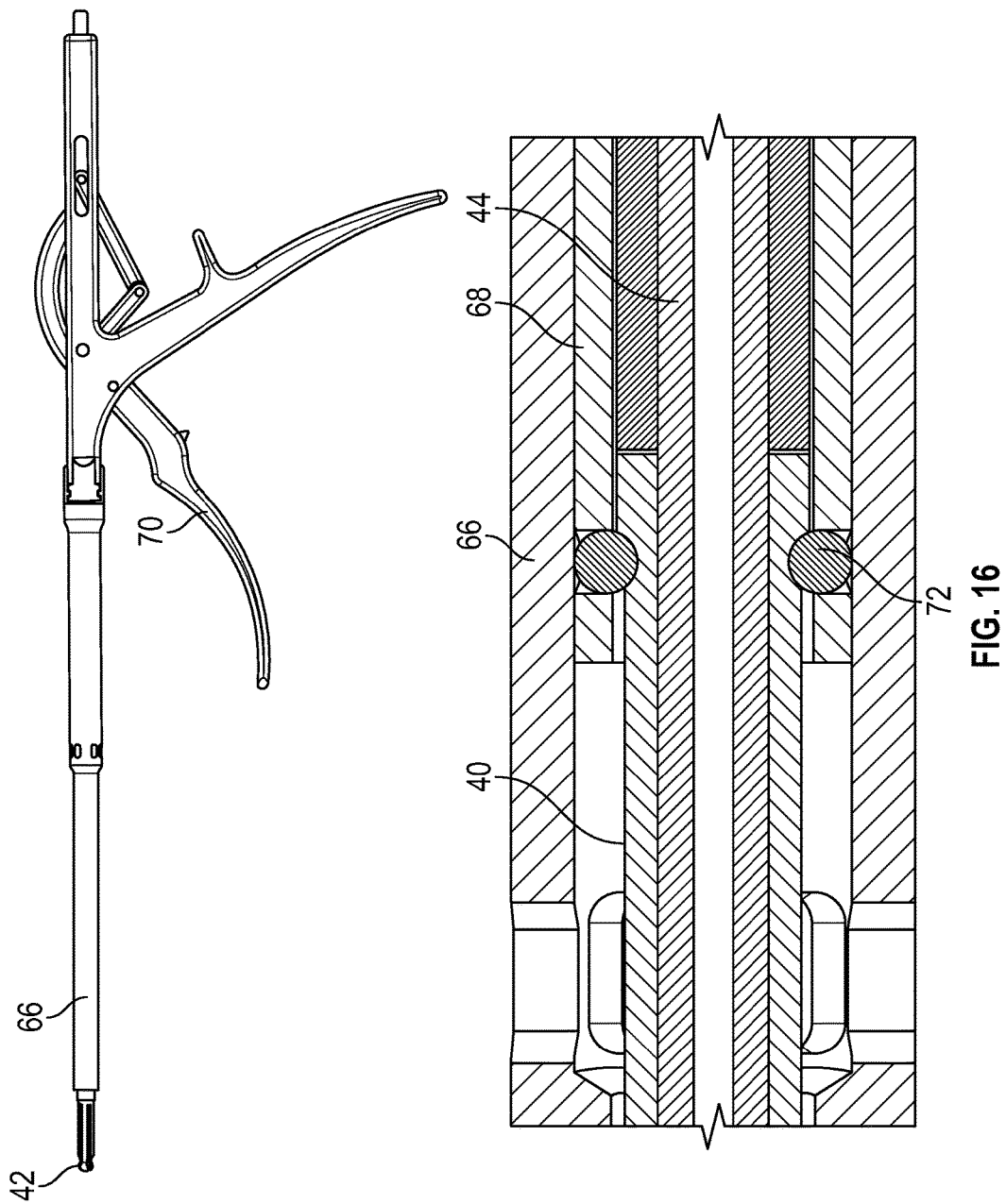
Figure 17:
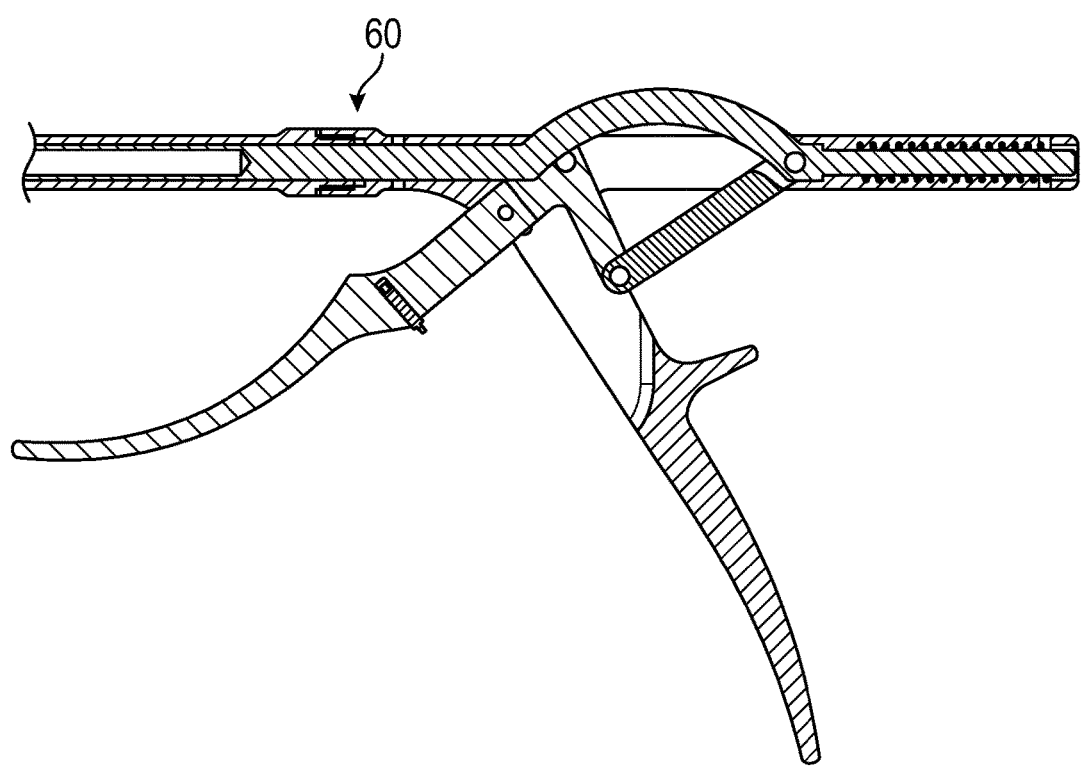
FIG. 17 shows a diagrammatical view of a pistol locker demonstrating one form of a bar linkage used to multiply force applied to handles of the pistol locker.

As with previously-described embodiments, a pistol locker is used as one example of an actuator to pull the pedicle screw into the locking bore of the rod coupler. The pistol locker of this embodiment accomplishes this by pulling up on the locking wand while simultaneously pushing down on the top of the rod coupler. FIGS. 14 and 17 illustrate certain features of an exemplary pistol locker 60. The distal end of the pistol locker 60 interfaces with the top of the rod coupler. In this embodiment the interface of the distal end includes a cylindrical region 62 sized to mate with an inner bore of the rod coupler, and a shoulder 64 sized to rest on top of the rod coupler, as shown in FIG. 14.

The pistol locker 60 also includes a mechanism for attaching the pistol locker 60 to the locking wand. The pistol locker 60 pulls up on the locking wand while the interface of the distal end remains relatively fixed, effectively pushing down on the rod coupler. Because the locking wand is attached to the pedicle screw via the collapsible tip (in its rigid configuration), the locking wand pulls the pedicle screw into the rod coupler, causing the press or interference fit as described in the applications incorporated herein by reference.

In this embodiment, the locking wand is fed into an outer barrel 66 of the pistol locker 60, continuing to a movable inner barrel 68. When a trigger 70 of the pistol locker 60 is fully extended (FIGS. 14 and 15), captive bearings 72 in the inner barrel 68 are free to translate radially in grooves cut in the outer barrel 66, allowing the locking wand to be inserted and removed. When the trigger 70 of the pistol locker 60 is pulled (FIG. 16), the inner barrel 68 of the pistol locker 60 translates, and the captive bearings 72 become constrained between the outer barrel 66 and the locking wand, causing them to engage with the locking wand. As the trigger 70 is pulled further, the locking wand is forced to translate with the inner barrel 68 of the pistol locker 60.

The pistol locker 60 provides a mechanism for pulling on the locking wand with significant mechanical advantage. The force required to lock the rod coupler to the pedicle screw via a press fit or interference fit as more fully described in the applications incorporated herein by reference is significant. To achieve the necessary force requires the use of a mechanism to generate significant mechanical advantage. The trigger 70 of the pistol locker 60 is coupled to the inner barrel 68 by a kinematic mechanism, as illustrated in FIG. 17, which converts the rotational motion of the trigger 70 into a force amplified linear motion of the inner barrel 68. In the specifically illustrated embodiment, the kinematic mechanism is a four-bar change-point crank slider.

FIGS. 18-21 illustrate a method for using the system and tools illustrated in FIGS. 11-17. For simplicity, FIGS. 18-21 illustrate a single pedicle screw, though in practice two pedicle screws would be in place at the time of locking the rod coupler to the pedicle screw, and each pedicle screw would have its own locking wand (reference may be made to FIGS. 7-10 for a similar configuration of a different embodiment).

Figure 18:
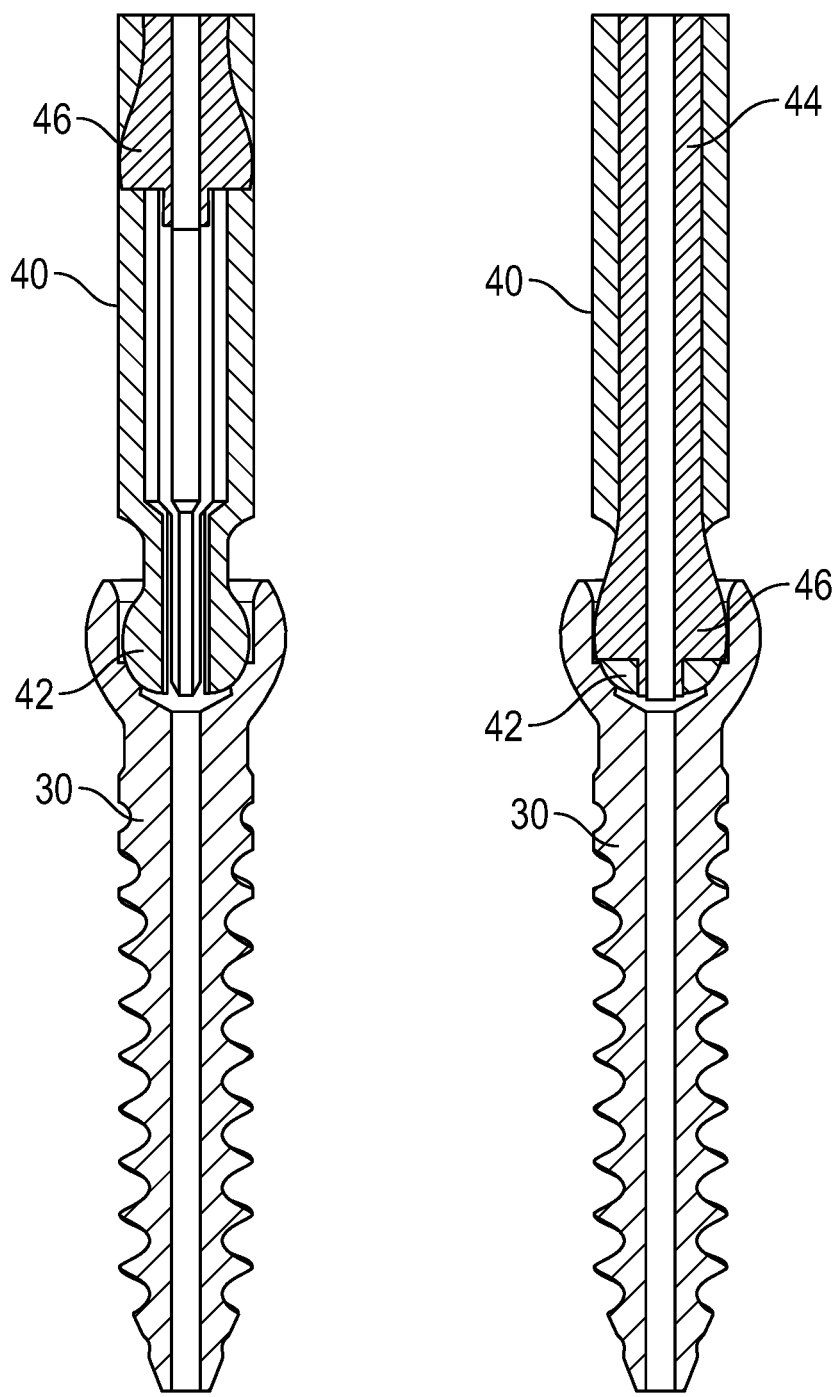
FIGS. 18-21 show views demonstrating use of a tool to couple components of a surgical construct.

Initially, as illustrated in FIG. 18, the collapsible tip 42 is inserted into and engages with a pedicle screw 30 with the elongate shaft 44 in its withdrawn state such that the driving feature 46 is not located within the collapsible tip 42. This allows the collapsible tip 42 to collapse and enter the pedicle screw 30. Then, the elongate shaft is pushed distally down the hollow rod 40 until the driving feature 46 is within the collapsible tip 42, whereupon the collapsible tip 42 is in its rigid configuration with the driving feature 46 engaging a corresponding driving feature of the pedicle screw 30.

Figure 19:
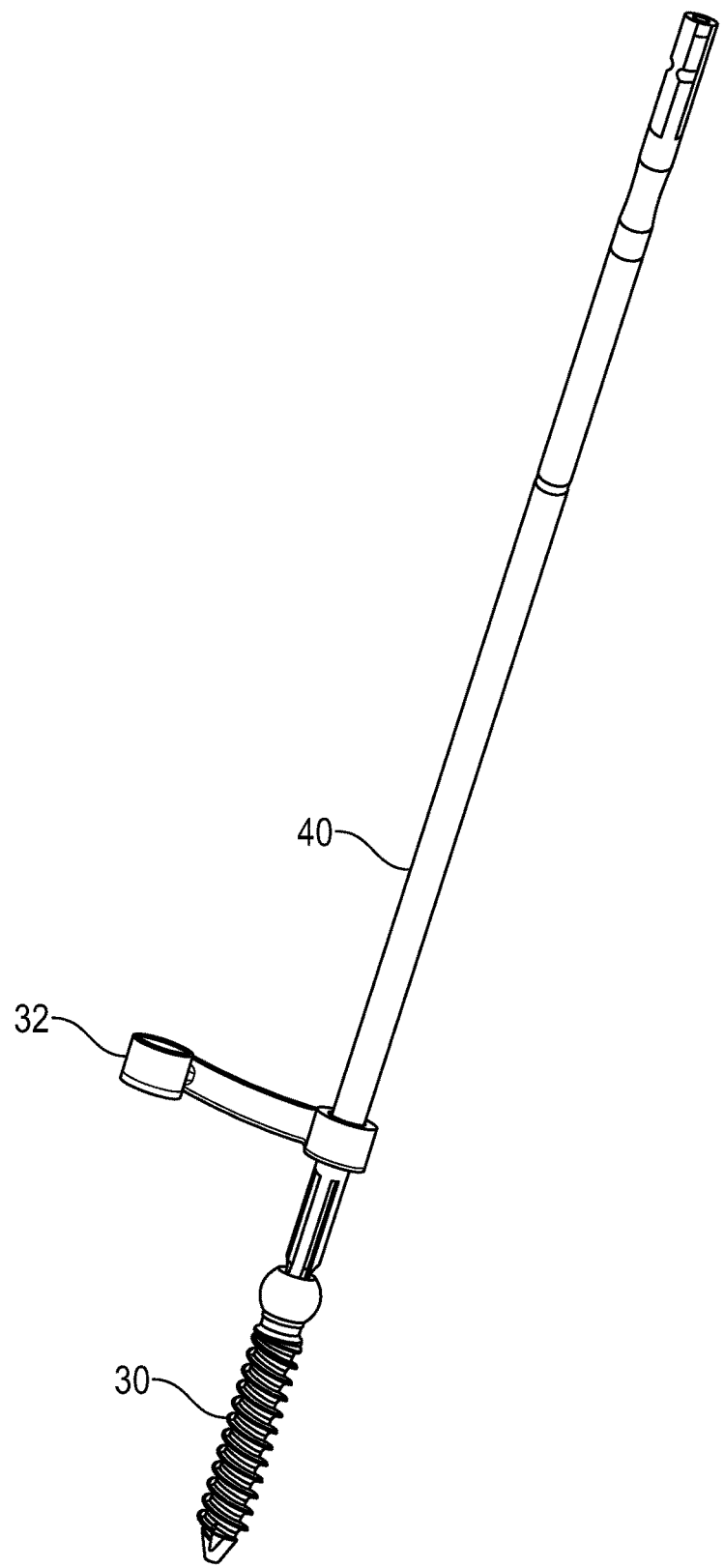

The surgeon then uses a driver handle that attaches to the locking wand to drive the pedicle screw into the prepared pedicle. The pedicle is not shown in the Figures, but the pedicle screw 30 is assumed to be in its final placement in the remaining Figures. The surgeon then repeats these steps with the other pedicle screw. As with the previously described embodiments, the surgeon then determines the proper rod length using a measuring device, such as a Vernier caliper, that holds the two locking wands parallel to each other (not shown, but compare by reference FIGS. 7-10). The selected rod coupler 32 is then placed over the locking wands and is slid down the locking wands to the pedicle screws 30, as shown in FIG. 19.

Figure 20:
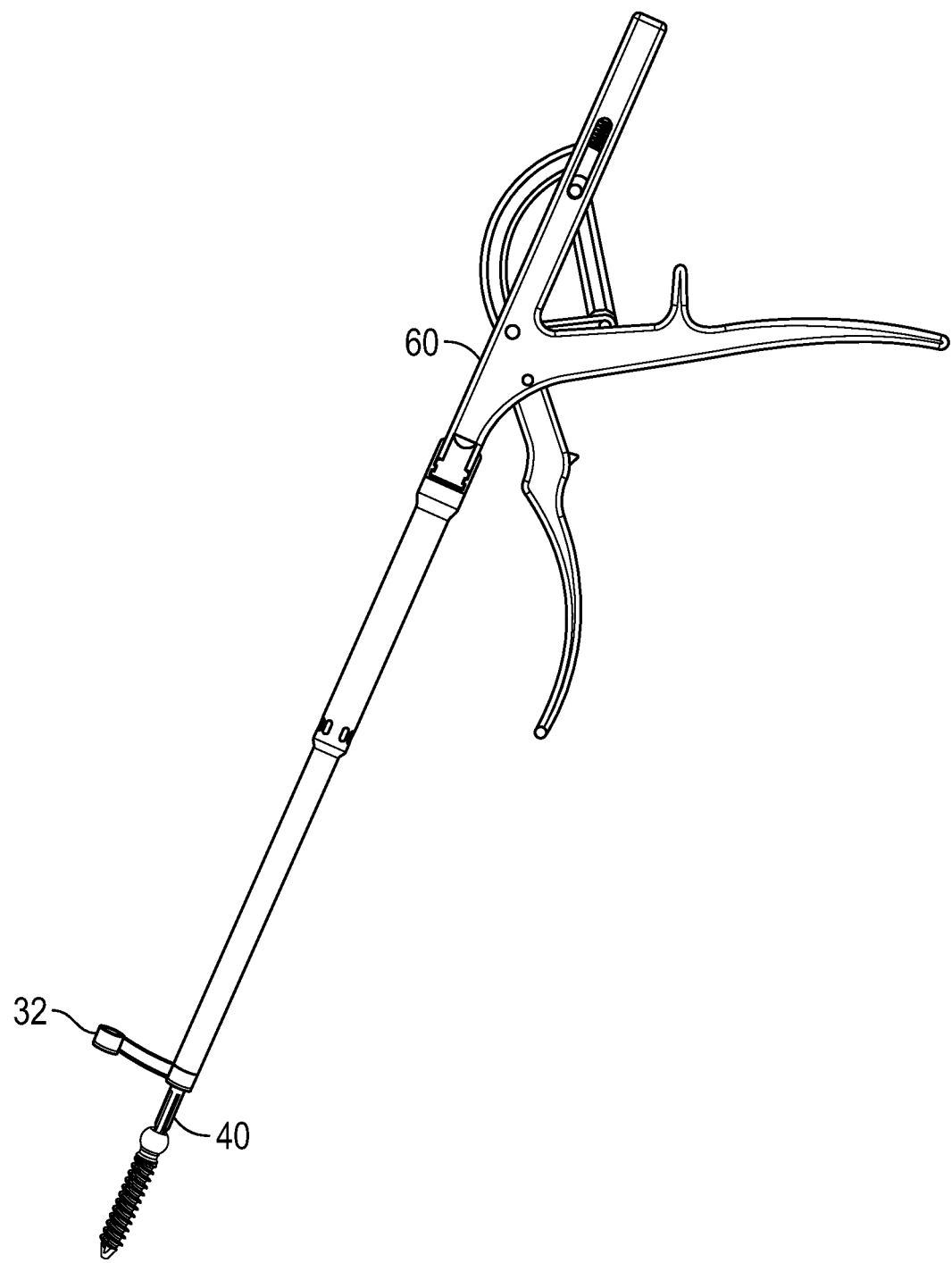
Figure 21:
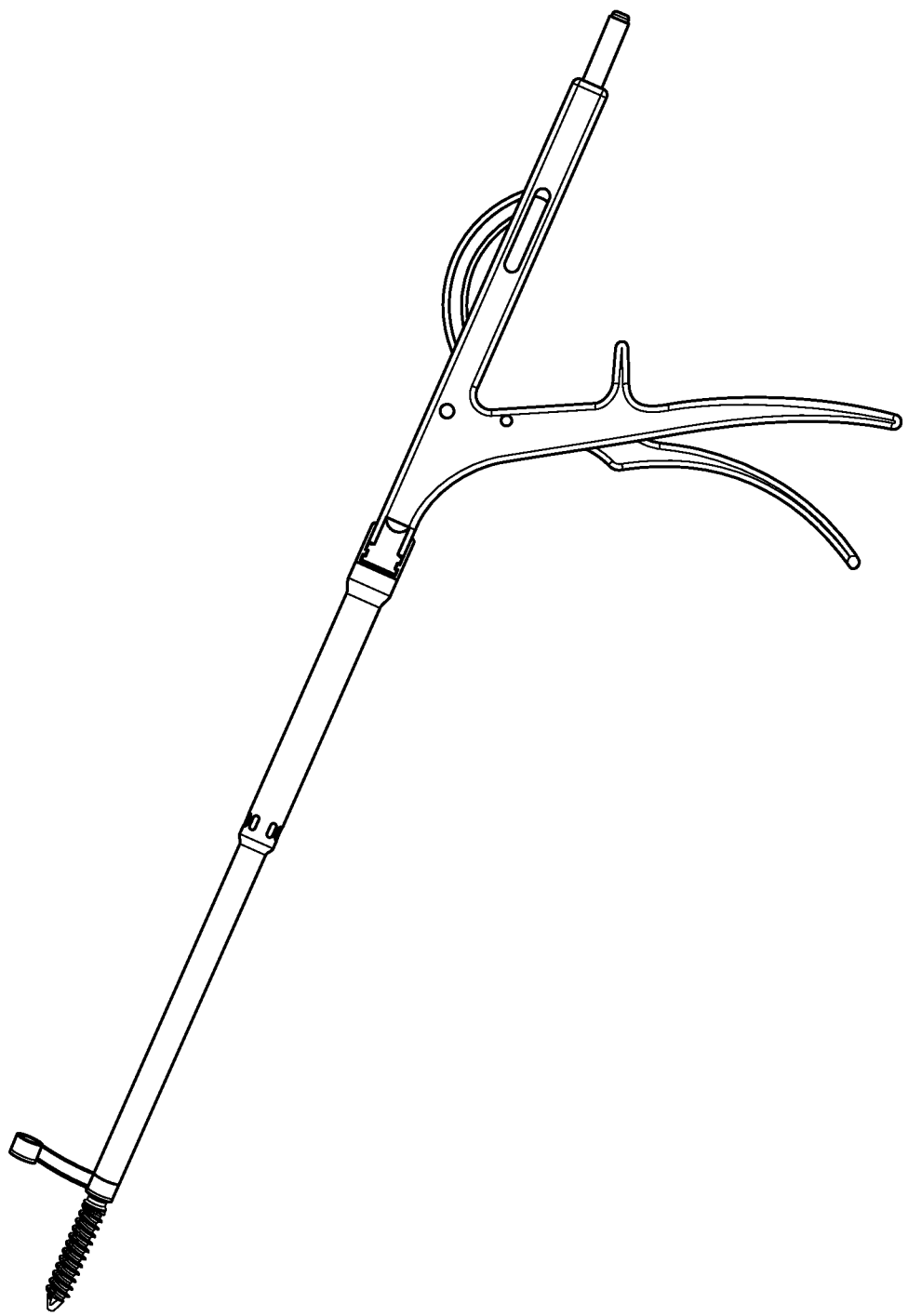

Next, the surgeon slides the pistol locker 60 over the first locking wand, as shown in FIG. 20, pushing down to ensure the rod coupler 32 contacts the pedicle screw 30. The surgeon then fully pulls the trigger 70 of the pistol locker 60 to engage the locking wand and to press the rod coupler 32 onto the pedicle screw 30, creating the press fit or interference fit previously described and as illustrated in FIG. 21. The surgeon then fully extends the trigger 70 to release the locking wand, pulls the pistol locker 60 off the locking wand, and repeats the steps on the other locking wand to lock the rod coupler 32 to the other pedicle screw. The surgeon then pulls on the proximal ends of each of the elongate shafts 44, allowing the collapsible tips 42 to collapse so the locking wands can be removed from the pedicle screws. The surgical site is then closed using conventional methods.

The present invention may be embodied in other specific forms without departing from its spirit or essential characteristics. The described embodiments are to be considered in all respects only as illustrative and not restrictive. The scope of the invention is, therefore, indicated by the appended claims, rather than by the foregoing description. All changes which come within the meaning and range of equivalency of the claims are to be embraced within their scope.

What is claimed and desired to be secured by Letters Patent is:

1. A tool for use in coupling components of a surgical construct comprising:
   an elongate hollow rod having a collapsible distal tip adapted to collapse to allow insertion into a surgical screw and further adapted to expand and engage a female cavity of the surgical screw to prevent withdrawal of the distal tip from the female cavity of the surgical screw;
   an elongate shaft slidingly disposed within the elongate hollow rod, the elongate shaft having a distal end comprising a driving feature adapted to engage a corresponding driving feature of the female cavity of the surgical screw; and a locking mechanism to prevent the distal end of the elongate shaft from being inadvertently removed from the distal tip of the elongate hollow rod.

2. The tool as recited in claim 1, wherein the locking mechanism comprises a mechanism selected from the group of:

corresponding snap fit engagement contours formed on the elongate hollow rod and the elongate shaft;
a spring loaded push button release;
a twist cam lock;
a Morse taper interface; and
a friction fit.

3. The tool as recited in claim 1, wherein the elongate hollow rod and the elongate shaft together form a locking wand, and wherein the locking wand comprises a proximal end having an interface for allowing a driver to transmit a rotational force to the locking wand and thus to any engaged surgical screw.

4. The tool as recited in claim 3, further comprising an elongate hollow sleeve adapted to slidingly receive the locking wand therein and to permit application of a force to two components of a surgical construct via the locking wand and the elongate hollow sleeve.

5. The tool as recited in claim 4, wherein the two components of the surgical construct are a pedicle screw and a rod adapted to extend between two pedicle screws.

6. The tool as recited in claim 4, further comprising an actuator adapted to generate relative movement between the locking wand and the elongate hollow sleeve.

7. The tool as recited in claim 6, further comprising a mechanism to reversibly engage the locking wand to the actuator.

8. The tool as recited in claim 7, wherein the mechanism to reversibly engage the locking wand to the actuator comprises captive bearings within the actuator and a corresponding groove on the locking wand.

9. The tool as recited in claim 7, wherein the actuator is a pistol locker.

10. The tool as recited in claim 9, wherein the pistol locker comprises a pair of handles operatively connected to a bar linkage mechanism adapted to multiply a force applied to the pair of handles and to transmit the multiplied force to generate the relative movement between the locking wand and the elongate hollow sleeve.

* * * * *